(12) United States Patent
Lynn et al.

(10) Patent No.: US 9,517,280 B2
(45) Date of Patent: Dec. 13, 2016

(54) ULTRAVIOLET DISINFECTION LIGHTING SYSTEM

(71) Applicant: American Air & Water, Inc., Hilton Head Island, SC (US)

(72) Inventors: William Warren Lynn, Hilton Head Island, SC (US); Steven Joseph Jackson, II, Hilton Head Island, SC (US)

(73) Assignee: American Air & Water, Inc., Hilton Head Island, SC (US)

( * ) Notice: Subject to any disclaimer, the term of this patent is extended or adjusted under 35 U.S.C. 154(b) by 155 days.

(21) Appl. No.: 14/472,628

(22) Filed: Aug. 29, 2014

(65) Prior Publication Data
US 2015/0062893 A1    Mar. 5, 2015

Related U.S. Application Data

(60) Provisional application No. 61/871,893, filed on Aug. 30, 2013.

(51) Int. Cl.
| | | |
|---|---|---|
| F21V 9/00 | (2015.01) | |
| A61L 2/10 | (2006.01) | |
| F21V 7/00 | (2006.01) | |
| F21V 23/00 | (2015.01) | |

(52) U.S. Cl.
CPC .. *A61L 2/10* (2013.01); *F21V 7/00* (2013.01); *F21V 23/003* (2013.01); *A61L 2202/14* (2013.01)

(58) Field of Classification Search
CPC ............ A61L 2/084; A61L 2/085; A61L 2/10; A61L 2202/14; F21V 7/00; F21V 7/0008; F21V 23/003

USPC ............... 362/217.01–217.17, 218–225, 227–248,362/249.02
See application file for complete search history.

(56) References Cited

U.S. PATENT DOCUMENTS

| | | | |
|---|---|---|---|
| 6,569,319 | B2 | 5/2003 | Kuennen et al. |
| 7,497,719 | B2 | 3/2009 | Ciancanelli et al. |
| 7,604,505 | B2 | 10/2009 | Zayas |
| 8,308,497 | B2 | 11/2012 | Zayas et al. |
| 8,350,228 | B2 | 1/2013 | Welker |
| 8,581,522 | B2 | 11/2013 | Inskeep |
| 2004/0074392 | A1 | 4/2004 | Choi |

(Continued)

OTHER PUBLICATIONS

International Search Report dated Dec. 18, 2014 for corresponding International App. No. PCT/US2014/053469.

(Continued)

*Primary Examiner* — Jason Moon Han
(74) *Attorney, Agent, or Firm* — Nelson Mullins Riley & Scarborough, LLP

(57) ABSTRACT

Germicidal light fixtures and germicidal light fixture systems. One embodiment of a germicidal light fixture includes a support structure and at least one first lighting device coupled with the support structure operative to emit ultraviolet radiation at a first predetermined wavelength. At least one second lighting device is coupled with the support structure and is operative to emit ultraviolet radiation at a second predetermined wavelength. The first and second predetermined wavelengths are selected such that ultraviolet radiation emitted from the at least one first lighting device and from the at least one second lighting device, respectively, is operative to inactivate microorganisms. At least one third lighting device is coupled with the support structure and is operative to emit visible radiation.

20 Claims, 16 Drawing Sheets

(56) References Cited

U.S. PATENT DOCUMENTS

| | | |
|---|---|---|
| 2006/0120929 A1 | 6/2006 | Ward et al. |
| 2008/0008620 A1 | 1/2008 | Alexiadis |
| 2009/0004046 A1 | 1/2009 | McEllen |
| 2010/0301768 A1 | 12/2010 | Chemel et al. |

OTHER PUBLICATIONS

Written Opinion of the International Searching Authority dated Dec. 18, 2014 for corresponding International App. No. PCT/US2014/053469.

| PATHOGEN | GROUP | ANNUAL CASES | PRIMARY INFECTION CAUSED | TYPE | MERV13 REMOVAL % | UVGI D90 J/m² |
|---|---|---|---|---|---|---|
| INFLUENZA A VIRUS | VIRUS | 2,000,000 | FLU, SECONDARY PNEUMONIA | COMMUNICABLE | 48 | 19.3 |
| MEASLES VIRUS | VIRUS | 500,000 | MEASLES (RUBEOLA) | COMMUNICABLE | 38 | (6) |
| STREPTOCOCCUS PNEUMONIAE | BACTERIA | 500,000 | LOBAR PNEUMONIA, SINUSITIS, MENINGITIS | COMMUNICABLE | 77 | 41.9 |
| STREPTOCOCCUS PYOGENES | BACTERIA | 213,962 | SCARLET FEVER, PHARYNGITIS | COMMUNICABLE | 86 | 22.0 |
| RESPIRATORY SYNCYTIAL VIRUS | VIRUS | 75,000 | PNEUMONIA, BRONCHIOLITIS | COMMUNICABLE | 37 | - |
| VARICELLA-ZOSTER VIRUS | VIRUS | 46,016 | CHICKENPOX | COMMUNICABLE | 37 | 39.3 |
| PARAINFLUENZA VIRUS | VIRUS | 28,900 | FLU, COLDS, CROUP, PNEUMONIA | COMMUNICABLE | 37 | - |
| MYCOBACTERIUM TUBERCULOSIS | BACTERIA | 20,000 | TUBERCULOSIS, TB | COMMUNICABLE | 72 | 10.8 |
| BORDETELLA PERTUSSIS | BACTERIA | 6,564 | WHOOPING COUGH | COMMUNICABLE | 39 | - |
| RUBELLA VIRUS | VIRUS | 3,000 | RUBELLA (GERMAN MEASLES) | COMMUNICABLE | 62 | - |
| STAPHYLOCOCCUS AUREUS | BACTERIA | 2,750 | STAPHYLOCOCCAL PNEUMONIA, OPPORTUNISTIC | ENDOGENOUS | 85 | 6.6 |
| PSEUDOMONAS AERUGINOSA | BACTERIA | 2,626 | PNEUMONIA | NONCOMMUNICABLE | 60 | 9.7 |
| KLEBSIELLA PNEUMONIAE | BACTERIA | 1,488 | OPPORTUNISTIC, PNEUMONIA | ENDOGENOUS | 74 | 42.0 |
| LEGIONELLA PNEUMOPHILA | BACTERIA | 1,163 | LEGIONNAIRE'S DISEASE, OPPORTUNISTIC | NONCOMMUNICABLE | 62 | 12.6 |
| HAEMOPHILUS INFLUENZAE | BACTERIA | 1,162 | MENINGITIS, PNEUMONIA, ENDOCARDITIS | COMMUNICABLE | 41 | 35.1 |
| HISTOPLASMA CAPSULATUM | FUNGAL SPORE | 1,000 | HISTOPLASMOSIS, FEVER, MALAISE | NONCOMMUNICABLE | 99 | 93.2 |
| ASPERGILLUS | FUNGAL SPORE | 666 | ASPERGILLOSIS, ALVEOLITIS, ASTHMA | NONCOMMUNICABLE | 99 | 1000 |
| SERRATIA MARCESCENS | BACTERIA | 479 | BACTEREMIA, ENDOCARDITIS, PNEUMONIA | ENDOGENOUS | 72 | 10.0 |
| ACINETOBACTER | BACTERIA | 147 | OPPORTUNISTIC/SEPTIC, MENINGITIS | ENDOGENOUS | 94 | 10965 |
| CORYNEBACTERIUM DIPHTERIAE | BACTERIA | 10 | DIPHTHERIA, TOXIN PRODUCED | COMMUNICABLE | 76 | 32.8 |
| SARS VIRUS | VIRUS | 10 (CHINA) | SEVERE ACUTE RESPIRATORY SYNDROME | COMMUNICABLE | 45 | 226.0 |
| HAEMOPHILUS PARAINFLUENZAE | BACTERIA | COMMON | CONJUNCTIVITIS, PNEUMONIA, MENINGITIS | ENDOGENOUS | 98 | (38) |
| BURKHOLDERIA CENOCEPACIA | BACTERIA | COMMON | OPPORTUNISTIC | NONCOMMUNICABLE | 77 | 58.0 |
| CRYPTOCOCCUS NEOFORMANS | FUNGAL SPORE | COMMON | CRYPTOCOCCOSIS, CRYPTOCOCCAL MENINGITIS | NONCOMMUNICABLE | 99 | 138 |
| CHLAMYDIA PNEUMONIAE | BACTERIA | RARE | PNEUMONIA, BRONCHITIS, PHARYNGITIS | COMMUNICABLE | 65 | - |
| COCCIDIODES IMMITIS | FUNGAL SPORE | RARE | COCCIDIOIDOMYCOSIS, VALLEY FEVER | NONCOMMUNICABLE | 99 | - |
| NOCARDIA ASTEROIDES | BACTERIAL SPORE | RARE | NOCARDIOSIS | NONCOMMUNICABLE | 93 | 187 |
| NOCARDIA BRASILIENSIS | BACTERIAL SPORE | RARE | NOCARDIOSIS | NONCOMMUNICABLE | 97 | - |
| ALCALIGENES | BACTERIA | RARE | OPPORTUNISTIC INFECTIONS, ENDOCARDITIS | ENDOGENOUS | 81 | - |
| BLASTOMYCES DERMATITIDIS | FUNGAL SPORE | RARE | BLASTOMYCOSIS, GILCHRIST'S DISEASE | NONCOMMUNICABLE | 99 | 93.2 |
| BURKHOLDERIA PSEUDOMALLEI | BACTERIA | RARE | MELIODOSIS, OPPORTUNISTIC | NONCOMMUNICABLE | 60 | (58) |
| CARDIOBACTERIUM | BACTERIA | RARE | OPPORTUNISTIC INFECTIONS, ENDOCARDITIS | ENDOGENOUS | 70 | - |
| MORAXELLA | BACTERIA | RARE | OTITIS MEDIA, OPPORTUNISTIC | ENDOGENOUS | 94 | 11513 |
| MUCOR PLUMBEUS | FUNGAL SPORE | RARE | MUCONNYCOSIS, RHINITIS | NONCOMMUNICABLE | 99 | 171 |
| PNEUMOCYSTIS CARINII | FUNGAL SPORE | RARE | PNEUMOCYSTOSIS | NONCOMMUNICABLE | 99 | - |
| RHIZOPUS STOLONIFER | FUNGAL SPORE | RARE | ZYGOMYCOSIS, ALLERGIC REACTIONS | NONCOMMUNICABLE | 99 | 267 |
| BURKHOLDERIA MALLEI | BACTERIA | RARE | GLANDERS, FEVER, OPPORTUNISTIC | NONCOMMUNICABLE | 74 | (58) |

FIG. 1

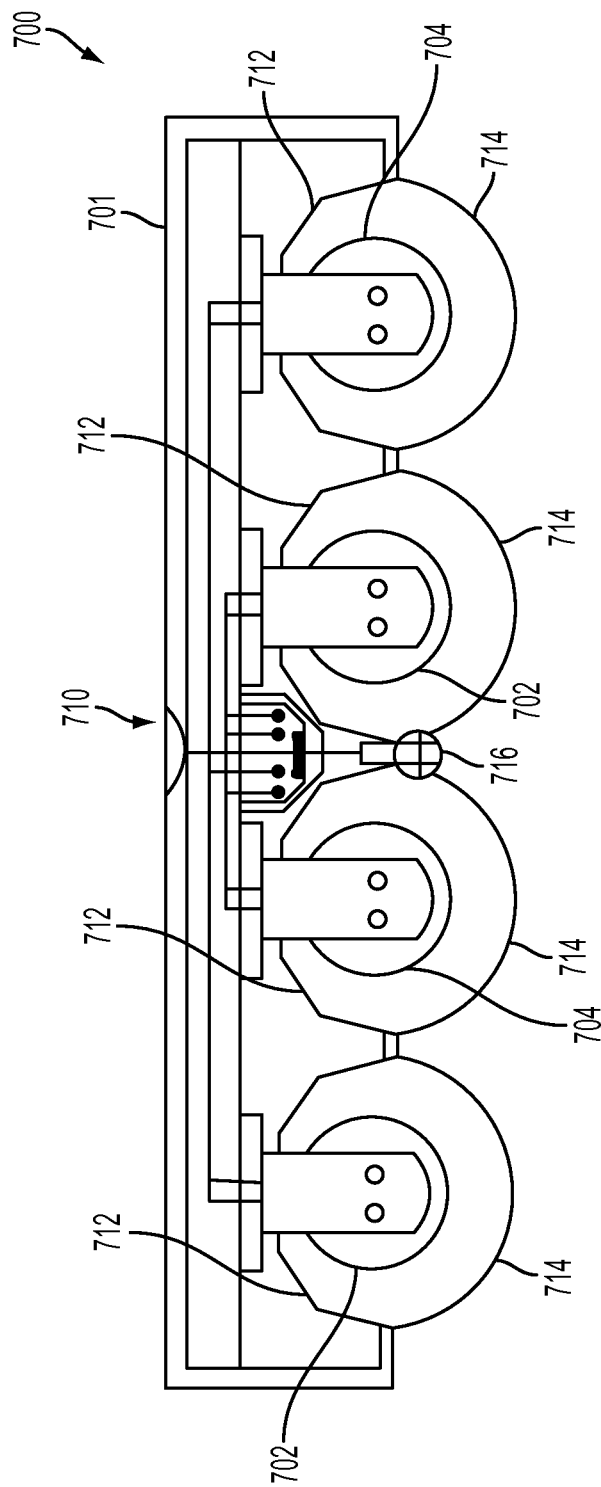

ULTRAVIOLET DISINFECTION LIGHTING SYSTEM

PRIORITY CLAIM

This application claims the benefit of U.S. Provisional Application Ser. No. 61/871,893, titled "Ultraviolet Disinfecting Lamp System and Fluorescent Lamp System," filed Aug. 30, 2013, which is hereby relied upon and incorporated herein by reference for all purposes.

FIELD OF THE INVENTION

The present invention relates generally to disinfection using ultraviolet germicidal irradiation (UVGI). More specifically, some embodiments of the present invention relate to an ultraviolet disinfecting lighting system comprising at least one ultraviolet light-emitting diode (UVLED) and/or at least one ultraviolet lamp for providing direct and indirect irradiation to inactivate microorganisms on at least one surface below the lighting system and in the air about the lighting system.

BACKGROUND

As is known, ultraviolet (UV) radiation emitted at certain wavelengths is mutagenic to microorganisms. Subtype C of the UV spectrum (UVC), also referred to as "germicidal" UV radiation, is generally considered to be radiation emitted at wavelengths in the range of 100-280 nanometers. In one application, UV radiation emitted at approximately 253.7 nanometers may be used to "inactivate" (i.e., destroy, render harmless, and/or prohibit the growth or reproduction of) certain microorganisms.

It is common to refer to a "dosage" of UVC radiation, a product of the UVC radiation intensity and exposure time, required to inactivate a particular microorganism. A dosage is typically measured in units of microwatt seconds per square centimeter ($\mu W \cdot s/cm^2$). Different dosages are required to inactivate different microorganisms. For example, a dosage of 12,100 $\mu W \cdot s/cm^2$ may be needed for a 3-log (99.9%) inactivation of methicillin resistant *Staphylococcus aureus* (MRSA), a dosage of 11,500 $\mu W \cdot s/cm^2$ may be needed for a 3-log inactivation of *clostridium difficile*, and a dosage of 8,400 $\mu W \cdot s/cm^2$ may be needed for a 3-log inactivation of vancomycin-resistant enterococci.

Prevention of infection by certain microorganisms is often an important concern in places where microorganisms may be widespread, including hospitals, laboratory settings, gyms, locker rooms, among many others. In a hospital operating room, for example, it may be important to inactivate microorganisms at the surgical site and on the many surfaces in the operating room, such as the operating table. This is often accomplished with the use of specialized UV lamp fixtures surface-mounted on the ceiling of the operating room. A variable transformer (Variac) is used to adjust the intensity of these lamps depending on whether surgery is occurring or whether it is desired to "bathe" the operating room in UV radiation. Alternatively or in addition, this may be accomplished via a mobile UV lamp system 10 disposed on a rolling base 12 and comprising a plurality of UV lamps 14, as shown in FIG. 2. One example of lamp system 10 may be the ARTZ Mobile Room Germicidal UVC Solution offered by American Air & Water, Inc. of Hilton Head Island, S.C.

Further, it may be important to inactivate microorganisms in the upper air, as convection currents can carry such microorganisms throughout the room. In this regard, FIG. 1 is a table describing various potentially airborne nosocomial pathogens. Targeting microorganisms in the air may be done using the mobile lamp system 10, described above, or using specialized UV lamp fixtures directly mounted on the walls of the operating room, typically at a height of approximately 8 feet. These lamp fixtures often operate at full intensity, even during surgical procedures. An example of a prior art, wall-mounted UVGI fixture 16 configured to inactivate microorganisms in the air is shown in FIG. 3. UVGI fixture 16, which as shown may be similar to the TB-W UVGI fixture offered by American Air & Water, Inc., may comprise adjustable louvers 18 to allow a user to direct the UV radiation in a desired direction.

SUMMARY

The present invention recognizes and addresses various considerations of prior art constructions and methods. According to one embodiment, the present invention provides a germicidal light fixture. The germicidal light fixture comprises a support structure and at least one first lighting device coupled with the support structure operative to emit ultraviolet radiation at a first predetermined wavelength. In some embodiments, at least one second lighting device is also coupled with the support structure and is operative to emit ultraviolet radiation at a second predetermined wavelength. The first and second predetermined wavelengths are selected such that ultraviolet radiation emitted from the at least one first lighting device and from the at least one second lighting device, respectively, is operative to inactivate microorganisms. At least one third lighting device is coupled with the support structure and is operative to emit visible radiation.

According to another embodiment, the present invention provides a germicidal light fixture system. The germicidal light fixture system comprises a support structure and a controller. At least one presence detection sensor is in electronic communication with the controller. The at least one presence detection sensor is operative to transmit a signal to the controller indicative of the presence of a person. At least one first lighting device is coupled with the support structure and is operative to emit ultraviolet radiation at a first predetermined wavelength. The first predetermined wavelength is selected such that the ultraviolet radiation emitted from the at least one first lighting device is operative to inactivate microorganisms. The at least one first lighting device has a first longitudinal axis. At least one reflector is coupled with the support structure, and the at least one reflector has a second longitudinal axis parallel with the first longitudinal axis. The at least one reflector is rotatable about the first longitudinal axis in response to the signal.

According to a further embodiment, the present invention provides a germicidal light fixture system. The germicidal light fixture system comprises a support structure, a controller in electronic communication with the support structure, and at least one presence detection sensor in electronic communication with the controller. The at least one presence detection sensor is operative to transmit a signal to the controller indicative of the presence of a person. At least one first lighting device is coupled with the support structure and is operative to emit ultraviolet radiation at a first predetermined wavelength. At least one second lighting device is coupled with the support structure and is operative to emit ultraviolet radiation at a second predetermined wavelength. The first and second predetermined wavelengths are selected such that the ultraviolet radiation emitted from the at least one first lighting device and from the at least one second lighting device, respectively, is operative to inactivate microorganisms. The controller is operative to deactivate the at least one first lighting device in response to the signal.

According to yet another embodiment, the present invention provides a germicidal light fixture comprising a support structure and at least one first lighting device coupled with the support structure operative to emit ultraviolet radiation at a first predetermined wavelength. The first predetermined wavelength is selected such that the ultraviolet radiation emitted from the at least one first lighting device is operative to inactivate microorganisms. The at least one first lighting device has a first longitudinal axis. At least one reflector is coupled with the support structure, and the at least one reflector has a second longitudinal axis parallel with the first longitudinal axis. The at least one reflector is rotatable about the first longitudinal axis.

Those skilled in the art will appreciate the scope of the present invention and realize additional aspects thereof after reading the following detailed description of preferred embodiments in association with the accompanying drawing figures.

BRIEF DESCRIPTION OF THE DRAWINGS

A full and enabling disclosure of the present invention, including the best mode thereof directed to one skilled in the art, is set forth in the specification, which makes reference to the appended drawings, in which:

FIG. 1 is a table describing various potentially airborne nosocomial pathogens.

FIG. 17A is a schematic cross-sectional elevation of a recessed troffer light fixture in accordance with another embodiment of the present invention.

Figure 2:
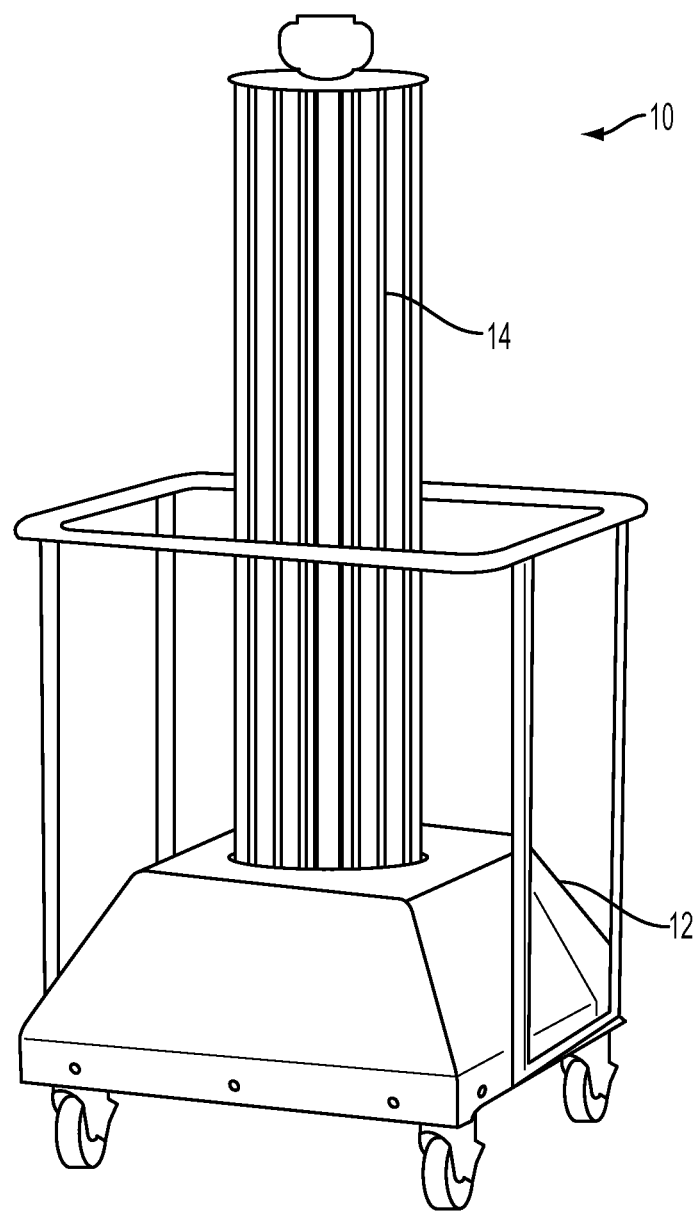
FIG. 2 is a perspective view of a prior art, mobile UV lamp system configured to inactivate microorganisms on surfaces and in the air.
Figure 3:
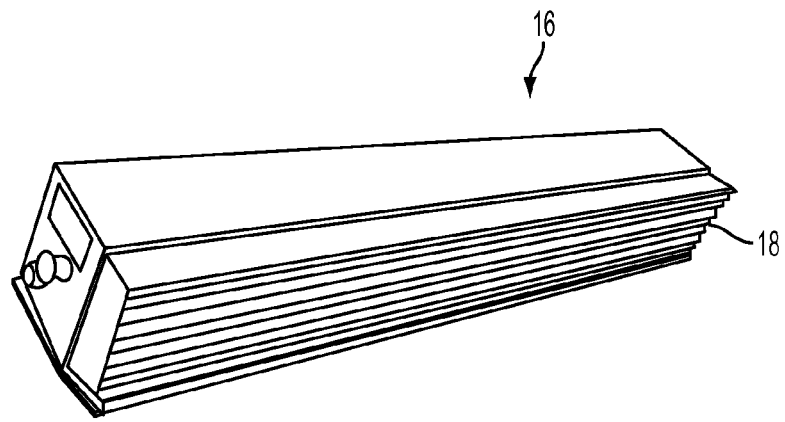
FIG. 3 is a prior art, wall-mounted UVGI fixture configured to inactivate microorganisms in the air.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the present disclosure including the appended claims and their equivalents.

In general, embodiments of the present invention provide a UV disinfecting lighting system. Although several preferred embodiments are described below in the context of an operating room environment, those of skill in the art will appreciate that the present invention is not so limited. In fact, embodiments of the present invention may be used in any environment in which germicidal lamp fixtures may be necessary or desirable, including hospitals, airports, hotels, airplanes, grocery stores, laboratory settings, gyms, restaurants, sports arenas, kitchens, buses, trains and train stations, banks, veterinary offices, cruise ships, classrooms, locker rooms, restrooms, offices, swimming pools, amusement parks, office buildings, retail stores, aquariums, manufacturing plants, warehouses, food processing centers, water purification centers, libraries, churches, museums, residences, bowling alleys, post offices, movie theaters, casinos, arcades, saunas, malls, gas stations, day care centers, laundromats, spas, barber shops, animal shelters, drinking fountains, ATMs, elevators and escalators, taxis, parking garages and livestock corrals, among many others. Likewise, embodiments of the present invention may be used with light fixtures other than recessed troffer fixtures, including pendant style fixtures.

Figure 4:
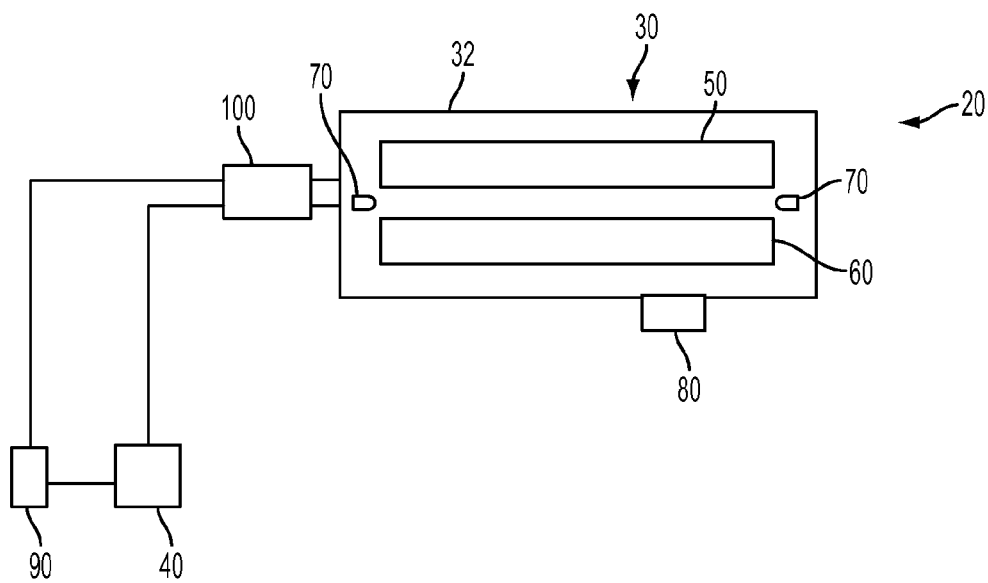
FIG. 4 is a schematic representation of a UV disinfecting lighting system in accordance with an embodiment of the present invention.

Referring now to FIG. 4, one embodiment of the present invention comprises a UV disinfecting lighting system 20. In general, UV disinfecting lighting system 20 may comprise a light fixture 30 in electrical communication with a switch 40. In a preferred embodiment, light fixture 30 may be a troffer light fixture comprising a housing 32 configured for recess mount in a ceiling, such as a suspended grid ceiling. However, other embodiments are contemplated in which the housing is mounted to the ceiling surface or suspended from the ceiling. Further, where system 20 is used in a livestock environment, the suspension of light fixture 30 may be operatively connected to a motor (e.g., a motorized winch) such that light fixture 30 may be lowered into a livestock corral when livestock are not present, but raised when livestock are present.

In any event, light fixture 30 preferably comprises a plurality of lighting devices, which in some embodiments include at least one conventional lamp or bulb and at least one UV lamp or bulb. For example, in the illustrated embodiment, light fixture 30 comprises lighting device(s) 50, which may be one or more conventional lamps or bulbs used for illumination of an area below light fixture 30, and lighting device(s) 60, which may be one or more UV lamps, UV bulbs, or UVLEDs for disinfecting a surface below light fixture 30. Also, UV disinfecting lighting system 20 may further comprise lighting device(s) 70, which may preferably be one or more UVLEDs or another UV lamp or bulb for inactivating microorganisms in the air. As described in more detail below, lighting devices 60 and 70 may be respectively positioned such that the light emitted by each lighting device propagates in different directions. For example, lighting devices 60 may be positioned such that the UV radiation emitted therefrom propagates substantially downward, providing direct irradiation of a surface beneath light fixture 30, but lighting devices 70 may be positioned such that the UV radiation emitted therefrom propagates substantially horizontally, i.e., generally along the plane in which lighting devices 50, 60 reside, rather than downward. Additionally, lighting system 20 may comprise a presence detection sensor 80 and a programmable timer 90. Sensor 80 and programmable timer 90 are preferably in electrical communication with lighting devices 50, 60 and switch 40.

Lighting devices 50 are operative to emit radiation therefrom that is visible to humans. In one embodiment, the visible radiation emitted from lighting devices 50 may have a wavelength in the range of about 400 nanometers to about 700 nanometers. Those of skill in the art are familiar with lighting devices 50 suitable for use in light fixture 30, but in one embodiment lighting devices 50 may preferably be long life T/5 fluorescent lamps. Notably, such lamps may provide energy savings in comparison to the use of traditional incandescent bulbs. In other embodiments, of course, other types of lamps may be used that are suitable for illuminating the environment in which lighting system 20 is located. These include, but are not limited to, incandescent lamps, compact fluorescent lamps, high-intensity discharge lamps, and LEDs. Lighting devices 60 are preferably configured to emit UV radiation at a sufficiently short wavelength to inactivate microorganisms, including bacteria, viruses, yeast, mold, and spores, using UV irradiation. In one embodiment, lighting devices 60 may be configured to emit UV radiation in the range of wavelengths corresponding to subtype C of the UV spectrum, i.e., 100-280 nanometers. In one preferred embodiment, lighting devices 60 may be a mercury vapor lamp which emits UV radiation at a wavelength of 253.7 nanometers. In other embodiments, lighting devices 60 may comprise pulsed xenon gas lamps which emit UV radiation at wavelengths between 200 and 320 nanometers. This is not required, however, and those of skill in the art can select lighting devices 60 which emit UV radiation at a suitable wavelength for particular germicidal applications. Those of skill in the art are familiar with commercially available UV lamps suitable for this purpose.

Lighting devices 50, 60 may preferably be driven by at least one ballast 100. Ballast 100 may be configured to operate at a voltage specific to lighting system 20 or may be multi-volt, configured for 120-277 volt power input, for example. Ballast 100 may also be a dimmable or variable ballast. Lighting system 20 may preferably include a ballast 100 for every two lighting devices 50, 60 it comprises. Further, in other embodiments, lighting system 20 may also comprise a variable transformer (not shown in FIG. 4) which, as noted above, may be used to adjust the intensity of lighting devices 60.

Switch 40, which may itself comprise a plurality of individual switches, is preferably configured to selectively illuminate each of lighting devices 50 and lighting devices 60. Further, switch 40 may be configured to selectively operate (e.g., turn "on" or "off") sensor 80 and programmable timer 90. More particularly, a user may sometimes desire to manually operate either or both of lighting devices 50, 60. For example, when it is not necessary to inactivate microorganisms but when a user needs illumination in the room, the user may use switch 40 to illuminate only lighting devices 50. Alternatively, when the user wishes to bathe an environment in UV radiation without being present, he or she may use switch 40 to activate only lighting devices 60. There may also be circumstances in which the user may use switch 40 to power both lighting devices 50 and lighting devices 60 because both illumination and inactivation of microorganisms are needed, such as during a surgical procedure in an operating room.

Notably, UV disinfecting lighting system 20 may also be programmed to operate for a predetermined time period. Specifically, a user may actuate switch 40 to power programmable timer 90 and motion sensor 80. The user may then program timer 90 to set a desired period of time in which lighting system 20, including either or both of lighting devices 50 and lighting devices 60, will operate. For example, it may be desirable to operate lighting devices 60 to inactivate microorganisms during a period of time when the environment in which lighting system 20 is located is not in use, such as late at night. Operating only lighting devices 60, rather than operating both lighting devices 60 and lighting devices 50, may also produce energy savings. In an operating room environment, such use of lighting system 20 may provide an additional layer of protection against acquired infections, in that microorganisms are inactivated even when a surgical procedure is not scheduled. The amount of time during which lighting devices 60 operate may depend on the type of microorganism targeted and the desired dosage. UV disinfecting lighting system 20 is preferably capable of deactivating many types of microorganisms very quickly, and thus in some embodiments the predetermined time period may be a matter of minutes. Moreover, because the effect of UV radiation is cumulative (i.e., UV radiation breaks down microorganism DNA on a cumulative basis), a desired dosage may be achieved via intermittent operation of lighting devices 60.

In one embodiment, programmable timer 90 may be a digital timer which may be mounted in or on a nearby wall. For example, programmable timer 90 may be similar to the MEW-DT1800 model programmable timer offered by MaxximaStyle, a division of the Panor Corporation. Those of skill in the art may select other suitable timers for programmable timer 90.

If during the predetermined time of operation a person enters the environment in which lighting system 20 is located, however, it may be desirable to deactivate at least lighting devices 60. Doing so, for example, may protect a person from exposure to unwanted UV radiation. In this regard, sensor 80 is preferably configured to cause deactivation of lighting devices 60 when it detects motion within a predetermined area beneath or around lighting system 20. In some embodiments, sensor 80 may also be configured to simultaneously cause activation of lighting devices 50 for illumination. When motion is no longer detected, sensor 80 may cause reactivation of lighting devices 60 and deactivation of lighting devices 50 (if activated). Again, because of the cumulative effect of UV radiation, temporary interruption of radiation by lighting devices 60 does not reduce the germicidal effectiveness of lighting system 20. If a user desires to return lighting system 20 to a manual mode of operation, he or she may do so using switch 40. Those of skill in the art are familiar with suitable motion sensors having the above-described functionality. In some embodiments, sensor 80 may be a Doppler radar sensor. Also, as discussed below, in other embodiments, sensors other than motion detection sensors may be used to determine whether lighting devices 60 (and, in some cases, lighting devices 70) should be illuminated based on the presence or absence of a human (or other animal) within the environment in which lighting system 20 is located.

It other embodiments, UV disinfecting lighting system 20 may also comprise a remote control in place of or in addition to programmable timer 90. In such a case, the remote control would preferably be in wireless electronic communication with light fixture 30 and/or programmable timer 90. For example, the remote control could be used to separately program a predetermined time during which UV disinfecting lighting system would operate, and it could likewise be used to selectively activate and deactivate each of lighting devices 50, 60. Those of skill in the art are familiar with remote control systems suitable for this application.

Figure 5:
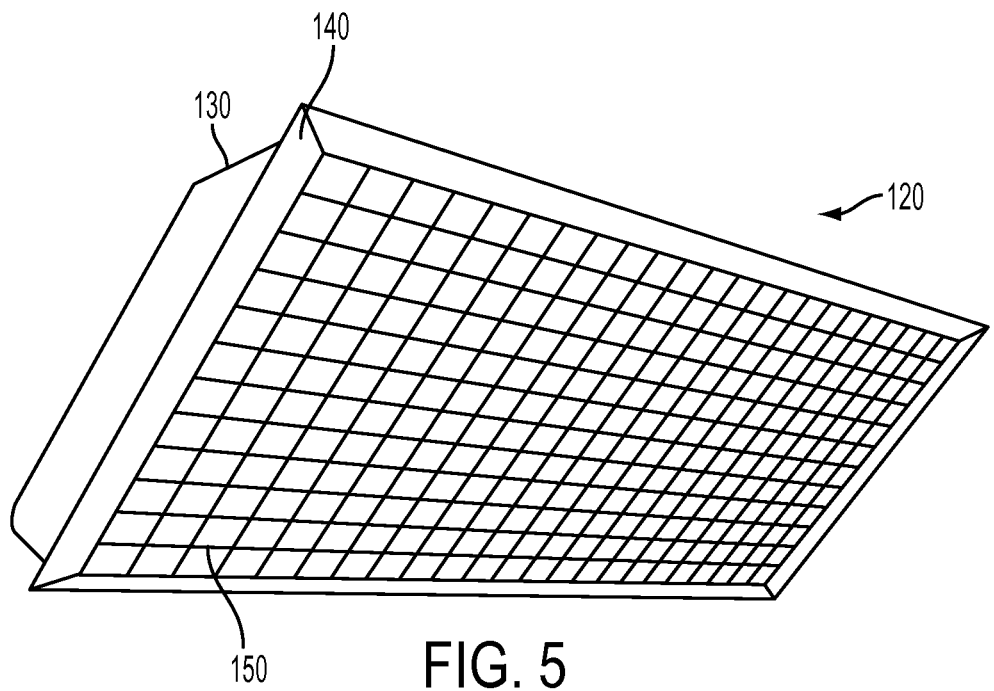
FIG. 5 is a perspective view of a recessed troffer light fixture configured for use with embodiments of the UV disinfecting lighting system of FIG. 4.

FIG. 5 is a perspective view of a recessed troffer light fixture 120 configured for use with embodiments of the UV disinfecting lighting system 20. Those of skill in the art are familiar with troffers, which are rectangular light fixtures typically sized to fit within one or more "cells" of a grid which forms a "dropped," or suspended, ceiling. The cells of the grid not filled with light fixtures are often filled with tiles or panels, as is well known. Thus, embodiments of the present invention may be readily "retrofit" in any of the many environments which are configured for lighting by recessed troffer light fixtures. Additional background information regarding recessed troffer light fixtures is provided in U.S. Pat. No. 8,350,228, the entire disclosure of which is incorporated by reference herein for all purposes.

Recessed troffer 120 may comprise a housing 130 and a flange 140 and may be formed of die-formed steel. When recessed troffer 120 is installed in a dropped ceiling, the majority of housing 130 may be concealed within the space between the dropped and actual ceilings, while flange 140 may be flush with the dropped ceiling. Although recessed troffer 120 is illustrated as a rectangular fixture, in other embodiments it may be square. Exemplary dimensions of recessed troffer 120 may be 2 feet by 4 feet, 2 feet by 2 feet, or 1 foot by 4 feet.

Figure 6:
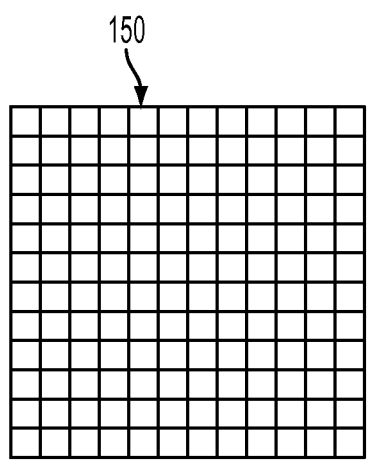
FIG. 6 is a schematic bottom plan view of the parabolic reflector grid of the recessed troffer light fixture of FIG. 5.

Recessed troffer 120 may also comprise a parabolic reflector grid 150. Referring now also to FIG. 6, a schematic bottom plan view of parabolic reflector grid 150 is illustrated. In general, parabolic reflector grid 150 may be a metal grid comprising a plurality of parabolic reflectors. As is well known, parabolic reflectors may be used to focus the energy emitted by lamps disposed within housing 130 into parallel beams oriented downwardly from recessed troffer 120. Thus, parabolic reflector grid 150 may be used to increase the intensity of the radiation emitted by recessed troffer 120.

Figure 7:
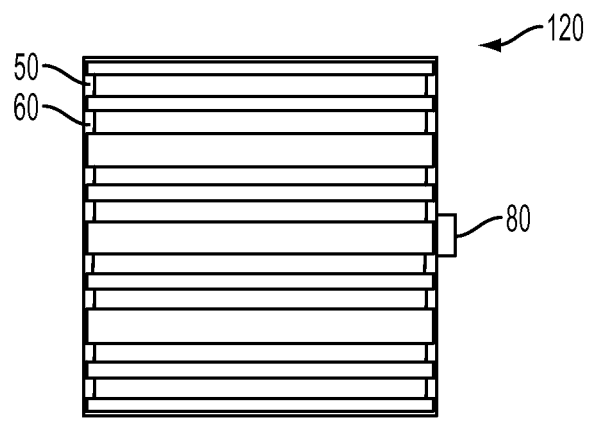
FIG. 7 is a schematic bottom plan view of the recessed troffer light fixture of FIG. 5 shown without the parabolic reflector grid of FIG. 6.

FIG. 7 is a schematic bottom plan view of recessed troffer light fixture 120, in this case shown without parabolic reflector grid 150 to illustrate some of the internal components of recessed troffer 120. In particular, recessed troffer 120 may comprise a plurality of lighting devices 50 and a plurality of lighting devices 60. In this case, lighting devices 50 are fluorescent lamps or bulbs and lighting devices 60 are UV lamps or bulbs. Four of each type of lighting devices 50, 60 are provided in this embodiment. As shown, lighting devices 50, 60 may be disposed in pairs and spaced along the width of recessed troffer 120, though this arrangement is not required. In one embodiment, lighting devices 50, 60 comprise a 4-pin end connector which is inserted into a complementary socket in recessed troffer 120, rather than a traditional 2-pin connector. Examples of such a 4-pin end connectors are shown in U.S. Pat. No. 7,497,719 to Ciancanelli et al. and U.S. Pat. No. 7,604,505 to Zayas, the entire disclosures of which are incorporated by reference herein for all purposes. In other embodiments, however, lighting devices 50, 60 comprise 2-pin connectors, such as those shown in U.S. Pat. No. 8,308,497, the entire disclosure of which is also incorporated by reference herein for all purposes, or a traditional 2-pin connector.

Sensor 80 may preferably be positioned on recessed troffer 120 so that it will detect motion or presence in a predetermined area, such as the room in which recessed troffer 120 is located or the area beneath troffer 120. As shown in FIG. 7, sensor 80 may be coupled with one side of recessed troffer 120. It will be appreciated, however, that sensor 80 may also be coupled with recessed troffer 120 in other suitable locations, such as on flange 140. Likewise, sensor 80 need not be positioned on recessed troffer 120 at all and may simply be in electrical communication therewith from another suitable or desired location.

Figure 8A:
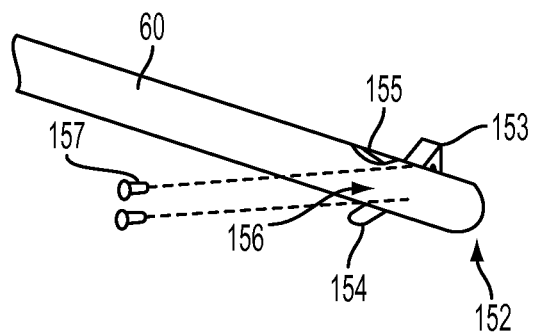
FIG. 8A is an enlarged schematic representation of the distal end of a UV lamp coupled with a clip for securing a lamp to a recessed troffer.
Figure 8B:
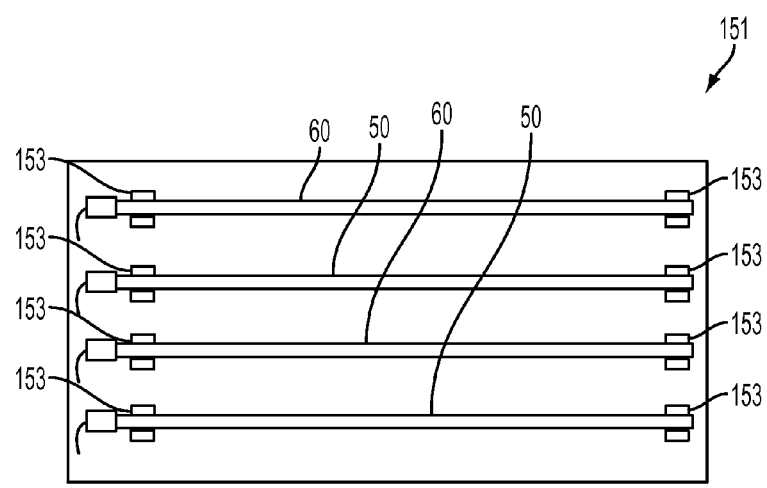
FIG. 8B is a schematic bottom plan view of a recessed troffer light fixture including four UV lamps secured therein using the clip of FIG. 8A.
Figure 8C:
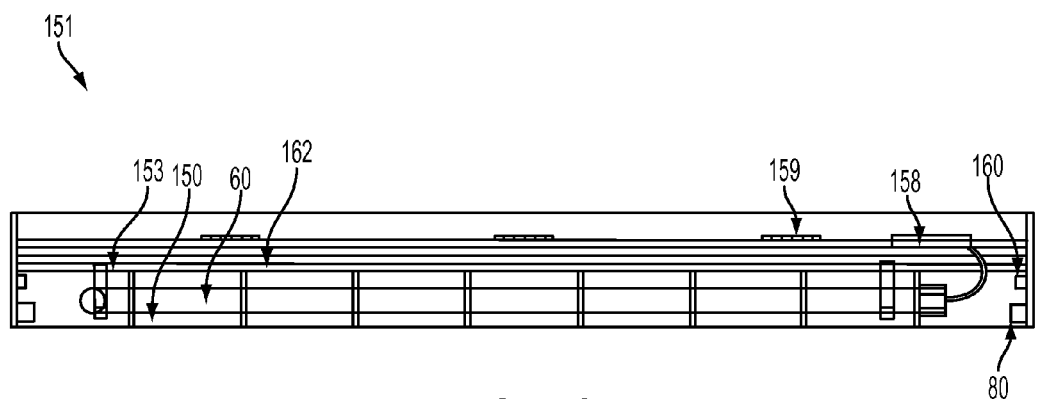
FIG. 8C is a left side elevation of the recessed troffer light fixture of FIG. 8B.
Figure 8D:
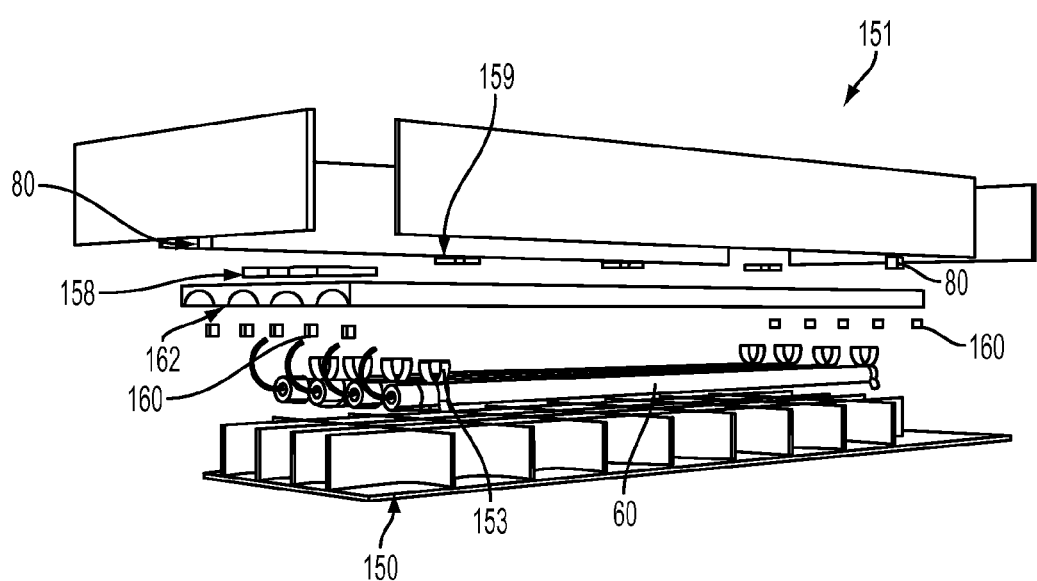
FIG. 8D is an exploded view of the recessed troffer light fixture of FIG. 8B.

FIGS. 8A-8D illustrate one preferred method for securing lighting devices 50, 60 in a recessed troffer 151. Recessed troffer 151 is preferably analogous to recessed troffer 120 in many respects, but in this embodiment recessed troffer 151 comprises two lighting devices 50 and two lighting devices 60, as shown in FIG. 8B. More particularly, FIG. 8A is an enlarged view of a distal end 152 of one of lighting devices 60. FIG. 8B is a schematic bottom plan view of recessed troffer light fixture 151. FIG. 8C is a side elevation of recessed troffer 151, and FIG. 8D is an exploded view of recessed troffer light fixture 151.

As shown in these figures, lighting devices 50, 60 may be coupled to recessed troffer 151 via clips 153. Referring now to FIG. 8A, clip 153, which in one embodiment may be a spring clip formed of stainless steel, preferably comprises two arms 154, 155 which together define an opening 156 sized to receive lighting device 60. When lighting device 60 is pressed into opening 156, arms 154, 155 may bias outward to snugly receive lighting device 60 therein. Clips 153 may be secured to recessed troffer via mounting hardware 157. Referring also to FIGS. 8B and 8C, it will be appreciated that another clip 153 may be provided to secure the proximal end of lighting device 60 to recessed troffer 151. Although clip 153 in FIG. 8A is described with respect to lighting device 60, one or more clips 153 are preferably be used to secure lighting devices 50 to recessed troffer 151 as well, as shown in FIG. 8B. However, it is noted that clips 153 are not required in all embodiments, as discussed in more detail below.

FIG. 8C also illustrates a ballast 158 in electrical communication with one of lighting devices 60. Preferably, ballast 158 is analogous to ballast 100 described above. As shown, ballast 158 may be mounted in an electrical compartment 159 in the top portion of recessed troffer 151.

As shown in FIGS. 8C and 8D, one or more fans 159 may be provided in recessed troffer 151. Preferably, fans 159 may be small, quiet fans to both cool the lighting devices of recessed troffer 151 and to force air circulation. In this regard, recessed troffer 151 may further comprise lighting devices 160, which in this embodiment may be UVLEDs. As discussed in more detail below, lighting devices 160 are preferably oriented such that UV radiation emitted therefrom propagates substantially horizontally, rather than vertically downward, so that microorganisms in the air about troffer 151 and on lighting devices 50, 60 may be inactivated. Further, fans 159 may both provide cooling to any or all of lighting devices 50, 60, and 160 and operate to draw air into the path of UV radiation emitted by lighting devices 160.

Figure 9:
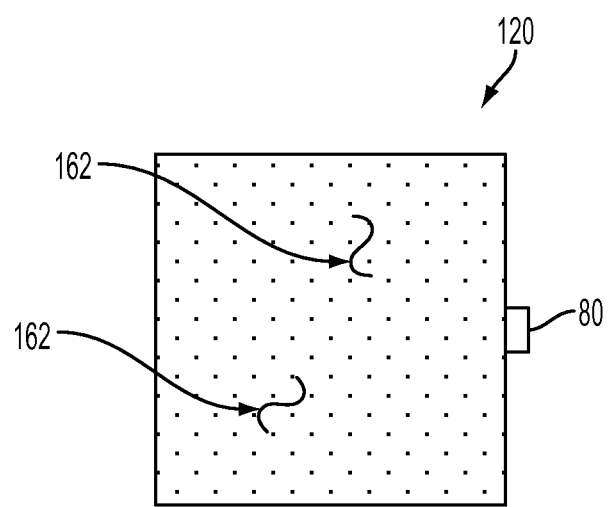
FIG. 9 is a schematic bottom plan view of the recessed troffer light fixture of FIG. 5 shown without lamps and having a reflective backing in accordance with an embodiment of the present invention.

Light fixture(s) of UV disinfecting lighting systems in accordance with embodiments of the present invention may also comprise a reflective backing to increase the intensity of lighting devices 50, 60. In this regard, FIG. 9 illustrates recessed troffer 120 without lighting devices 50, 60 and having a reflective backing 162 in accordance with an embodiment of the present invention. See also FIGS. 8C-8D. Reflective backing 162 may preferably comprise a layer of reflective anodized aluminum which covers the upper interior surface of the housing of troffer 120 behind lighting devices 50, 60. Additionally, reflective backing 162 may create either specular or diffuse reflection of light and UV radiation emitted from lighting devices 50, 60. One example of a suitable material for reflective backing 162 is the reflective aluminum "lighting sheet" offered by Anomet Inc. Those of skill in the art will appreciate that highly reflective materials other than reflective aluminum may be used for reflective backing 162.

Figure 10:
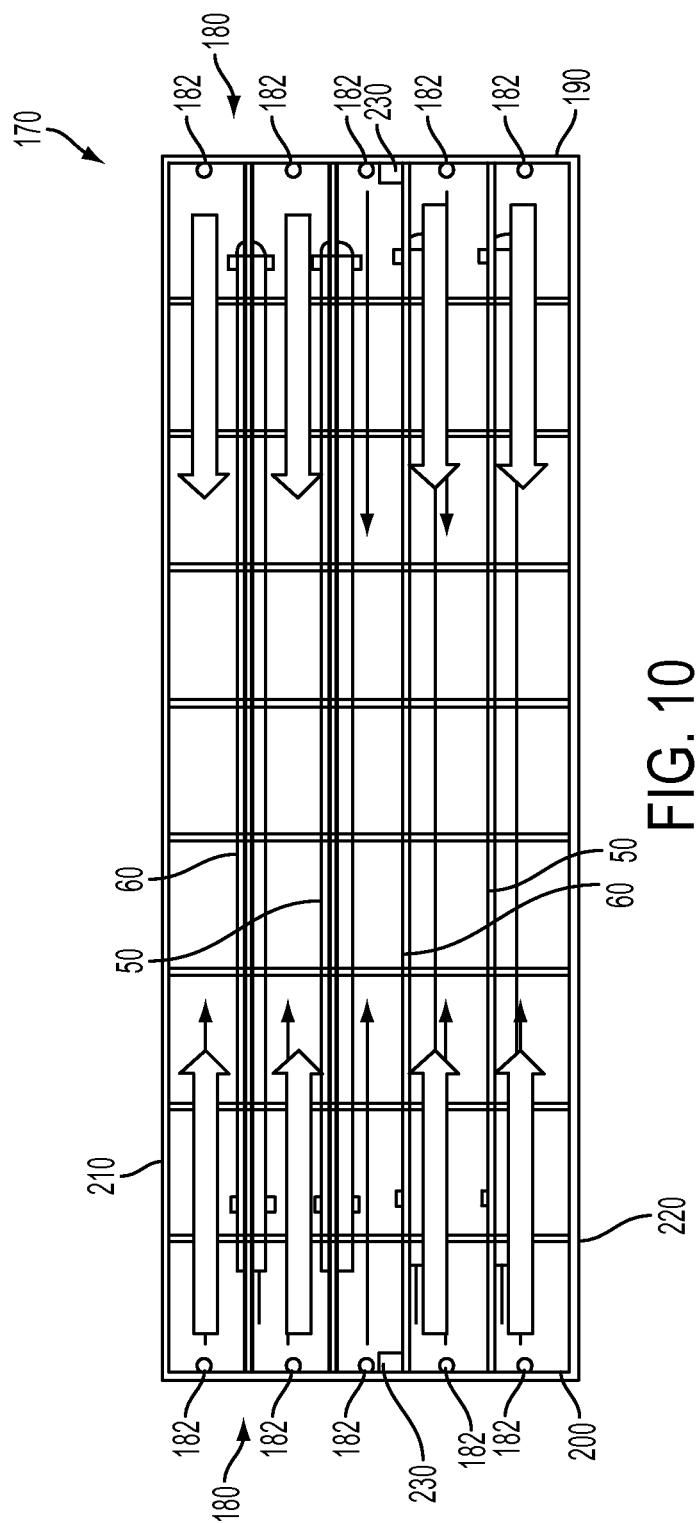
FIG. 10 is a schematic bottom plan view of a recessed troffer light fixture having a plurality of UVLEDs in accordance with another embodiment of the present invention.

FIG. 10 is a schematic bottom plan view of a recessed troffer light fixture 170 having a plurality of lighting devices 180 in accordance with another embodiment of the present invention. In this embodiment, lighting devices 180 may preferably be UVLEDs. Like recessed troffers 120 and 151, recessed troffer 170 is configured for use in a UV disinfecting lighting system analogous to system 20. In this regard, recessed troffer 170 may preferably be similar to recessed troffer 151 and preferably includes lighting devices analogous to either or both of lighting devices 50, 60 of recessed troffer 151.

Lighting devices 180, which in this embodiment may resemble traditional LEDs, each comprise a shell 182. Similar to lighting devices 60, lighting devices 180 are preferably configured to emit UV radiation at a sufficiently short wavelength to inactivate microorganisms, including bacteria, viruses, yeast, mold, and spores, using UV irradiation. In one embodiment, lighting devices 180 may be configured to emit UV radiation in the range of wavelengths corresponding to subtype C of the UV spectrum, i.e., 100-280 nanometers. In one embodiment, lighting devices 180 may emit UV radiation at a wavelength of 253.7 nanometers. Where lighting devices 180 are UVLEDs, it will be appreciated that lighting devices 180 may emit UV radiation at a wavelength between about 260 nanometers and about 280 nanometers. This is not required, however, and those of skill in the art can select lighting devices 180 which emit UV radiation at a suitable wavelength for germicidal applications. Those of skill in the art are familiar with commercially available UVLEDs suitable for this purpose.

In the illustrated embodiment, lighting devices 180 are equally spaced along the sides 190, 200 of recessed troffer 170 which include the sockets which receive lighting devices 50, 60. If recessed troffer 170 includes four UV lamps, for example, a lighting device 180 may be positioned beside each UV lamp. Alternatively, lighting devices 180 may be positioned at other locations on recessed troffer 170, such as above or below UV lamps or lamps used for illumination, or along the sides 210, 220 of recessed troffer 170 perpendicular to the sides which include lamp sockets. Recessed troffer 170 may also comprise a sensor 230 that is preferably analogous to sensor 80, described above.

Further, although recessed troffer 170 is shown having a plurality of UVLEDs, those of skill in the art will appreciate that recessed troffer 170 may have as few as one UVLED in some embodiments. Indeed, in other embodiments, recessed troffer 170 may have any combination of lighting devices 50, lighting devices 60, and lighting devices 180. In some embodiments, for example, lighting devices 50 may be LEDs (as noted above) and lighting devices 180 may be used in place of lighting devices 60.

Lighting devices 180 are preferably positioned to inactivate microorganisms in the air about recessed troffer 170, rather than on surfaces below recessed troffer 170 (though they still may do the latter). Thus, as shown by the directional arrows in FIG. 10, lighting devices 180 may be oriented substantially horizontally. In FIG. 10, for example, lighting devices 180 are oppositely disposed on sides 190, 200 and may be positioned such that the longitudinal axes of shells 182 are substantially parallel with the longitudinal axes of lighting devices 50 and 60. Thus, lighting devices 180 may emit UV radiation at the desired wavelength around and along the plane in which they are situated, thereby inactivating microorganisms which circulate in the air about recessed troffer 170, on inside surfaces of recessed troffer 170, and on the lighting devices included therewith. Those of skill in the art will appreciate, however, that lighting devices 180 need not be oriented horizontally in all embodiments, and they may inactivate microorganisms in the air about recessed troffer 170 while being oriented at other angles, including at an angle perpendicular to the plane in which the lamps of recessed troffer 170 are situated. In addition, in some embodiments certain of lighting devices 180 may be oriented at different angles than other of lighting devices 180. Notably, the use of lighting devices 180 within a UV disinfecting lighting system may eliminate the need to use one of the prior art systems for inactivating microorganisms in the air described above.

Further, also as described above, there may be circumstances in which a user desires to manually selectively operate the various lighting devices which may be provided in recessed troffer 170. Thus, a switch analogous to switch 40 may be provided. Additionally, like recessed troffer 120, recessed troffer 170 is preferably in electrical communication with a programmable timer so that the lamps and/or UV lamps of recessed troffer 170 may be programmed to operate at predetermined times. Notably, however, in one embodiment, lighting devices 180 may operate continuously, regardless of whether either or both of conventional lamps and UV lamps which may be provided in recessed troffer 170 are active. Although this mode of operation is not required, it provides inactivation of microorganisms in the air about recessed troffer 170 at all times. Thus it may be advantageous where air continues to circulate (and potentially spread microorganisms) in the environment in which recessed troffer 170 is located while any UV lamp(s) associated with recessed troffer 170 are inactive. As discussed above with reference to FIGS. 8C-8D, the UV disinfecting lighting system which comprises recessed troffer 170 may also comprise one or more fans to draw air over the lighting devices in recessed troffer 170 to aid in sterilization. Further, the lighting devices 180 in recessed troffer 170 may be cooled by such fans or, in other embodiments, by a dedicated cooling system.

Figure 11:
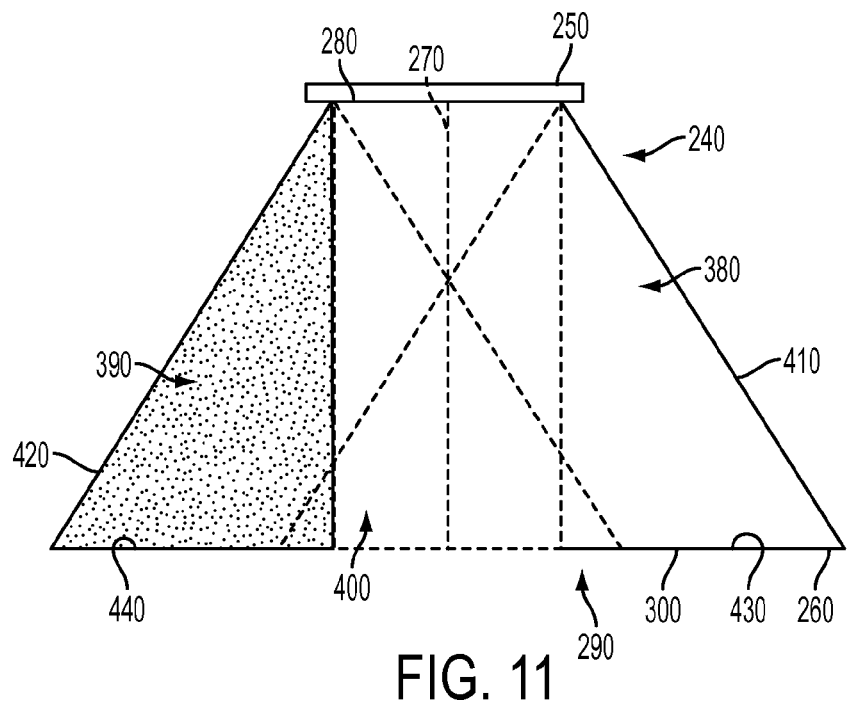
FIG. 11 is a schematic left side elevation of a volume irradiated by a UV lamp within a recessed troffer lighting fixture in accordance with an embodiment of the present invention.
Figure 12:
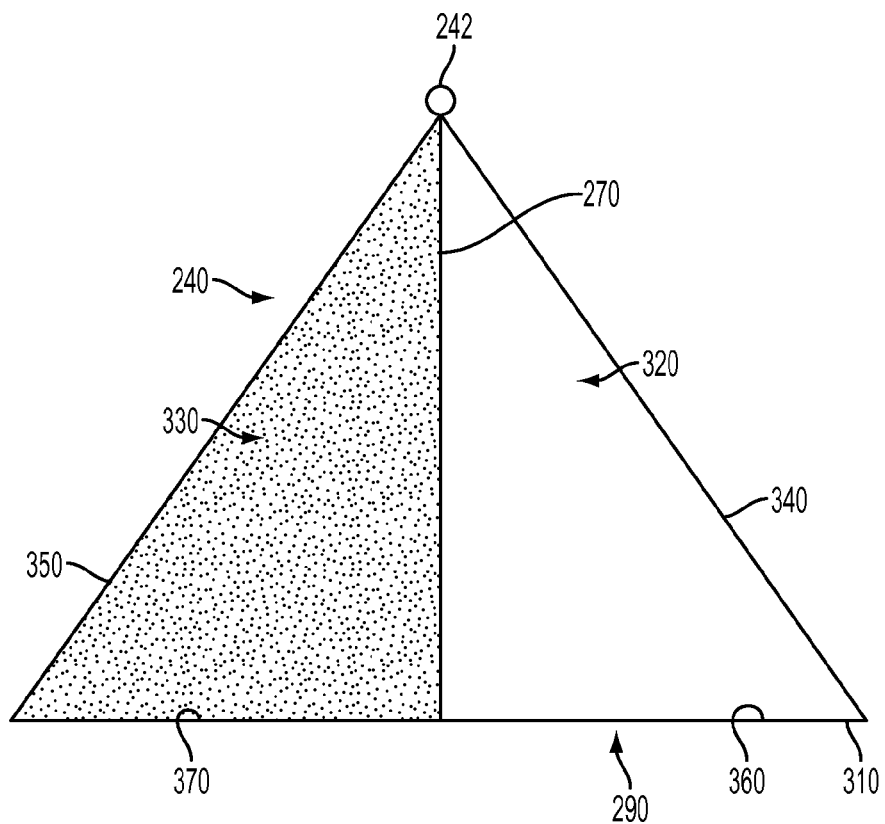
FIG. 12 is a schematic front elevation of the volume irradiated by the UV lamp within the recessed troffer lighting fixture of FIG. 11.

It may be desirable to approximate the area on a particular surface that will receive a predetermined dosage of UV radiation. In this regard, FIG. 11 is a schematic side elevation of a volume 240 irradiated by a UV lamp 242 (FIG. 12) in recessed troffer lighting fixture 250 in accordance with an embodiment of the present invention. FIG. 12 is a schematic front view of volume 240 irradiated by UV lamp 242. For the purposes of this description, recessed troffer 250 is preferably analogous to recessed troffers 120, 170 described above.

Referring to these figures, UV lamp 242 in recessed troffer 250 is illustrated suspended above a surface 260, which may for example be a floor, at a height dimension 270. UV lamp 242 may have a lamp length dimension 280. When UV lamp 242 is activated, there will be an area 290 on surface 260 which receives a predetermined dosage of UV radiation. Those of skill in the art may select the predetermined dosage by considering, among other factors, the amount of time needed or desired to operate UV lamp 242, the intensity of the UV radiation emitted by UV lamp 242, the distance between surface 260 and UV lamp 242, and the characteristics of the microorganisms it is desired to inactivate.

To simplify the analysis and to produce a rough approximation, area 290 may be thought of as rectangular in shape (though in practice area 290 may more closely resemble an oval or circle). Thus, area 290 may be defined by a length dimension 300 (FIG. 11) and a width dimension 310 (FIG. 12) on surface 260. When viewed from the front (FIG. 12), volume 240 may be simplified as an equilateral triangle composed of two adjacent right triangles 320, 330. Triangles 320, 330 have hypotenuses 340, 350 and bases 360, 370, respectively. Similarly, when viewed from the side (FIG. 11), volume 240 may be simplified as a trapezoid composed of two adjacent right triangles 380, 390 and a rectangle 400. The base of rectangle 400 is equal to lamp length dimension 280, and triangles 380, 390 have hypotenuses 410, 420 and bases 430, 440, respectively. The height of triangles 320, 330, 380, and 390 is equal to height dimension 270.

As indicated above, height dimension 270 is known. The length of hypotenuses 340, 350, 410, and 420 may also be determined based on measurement of the points on surface 260 beyond which the UV radiation delivers a dosage less than the predetermined dosage. For example, this may be done using a radiometer. From these parameters, it is a simple exercise using the Pythagorean theorem to determine the length of the bases of triangles 320, 330, 380, and 390 and, consequently, area 290. In particular, width dimension 310 may be determined by adding the length of the bases of triangles 320, 330. Likewise, length dimension 300 may be determined by adding the length of the bases of triangles 380, 390 and the lamp length dimension 280. Finally, area 290 which will receive at least the predetermined dosage of UV radiation is determined by multiplying width dimension 310 by length dimension 300.

Figure 13:
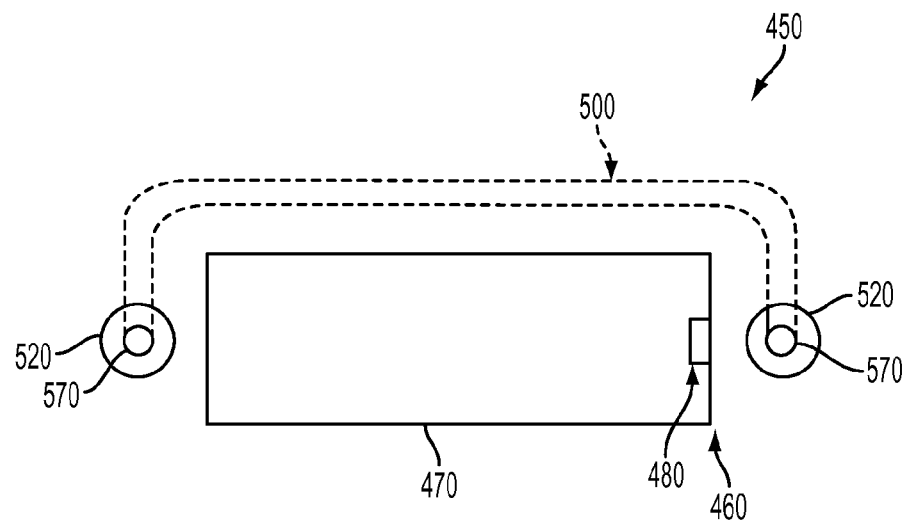
FIG. 13 is a schematic bottom plan view of an atomizer system configured for use with a UV disinfecting lighting system in accordance with another embodiment of the present invention.
Figure 14:
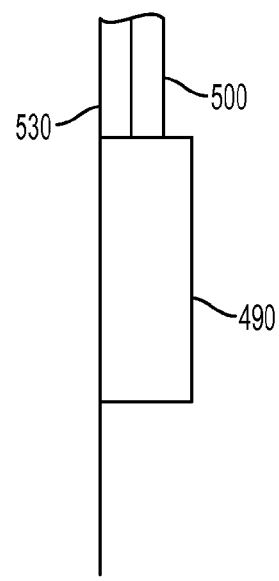
FIG. 14 is a schematic left side elevation of a hygienic fluid container configured for use with the atomizer system of FIG. 13.

FIGS. 13 and 14 illustrate a further embodiment of the present invention. In particular, FIG. 13 is a schematic bottom plan view of an atomizer system 450 configured for use with a UV disinfecting lighting system 460. UV disinfecting lighting system 460 is preferably analogous to lighting system 20 described above. Thus, it may preferably comprise one or more recessed troffer lighting fixtures 470, which are likewise preferably analogous to troffers 30, 120, 170, and 250 described above. For example, recessed troffer 470 may be coupled and in electrical communication with a motion sensor 480, or another suitable presence detection sensor as described herein. FIG. 14 is a schematic side elevation of a hygienic fluid container 490 configured for use with atomizer system 450.

More particularly, atomizer system 450 is preferably configured to disperse a liquid agent for hygienic and/or sanitary purposes. This may be desirable in certain environments, such as operating rooms, and those of skill in the art can select a suitable hygienic fluid for a particular environment. Atomizer system 450 may comprise tubing 500 in fluid communication with at least one atomizer nozzle 510 and with fluid container 490. As shown in FIG. 13, tubing 500 may extend above recessed troffer 470 within the space between a dropped ceiling and the actual ceiling of a particular environment. Atomizer nozzles 510, which may comprise fine atomizing spray tips, may be disposed within apertures 520 in the dropped ceiling. Atomizer nozzles 510 are preferably oriented perpendicularly to the dropped ceiling and may be flush therewith or extend slightly therefrom. As shown in FIG. 13, although atomizer nozzles 510 may be located at any location in a given environment, it may be desirable to locate atomizer nozzles 510 proximate to recessed troffer 470, for example on opposing sides thereof, for optimum coverage. It is typically desirable to avoid dispersing liquid within recessed troffer 470, though in some embodiments atomizer nozzles 510 may be located within recessed troffer 470. For example, atomizer nozzles 510 may be centered towards the bottom face of troffer 470 in between each lighting device thereof.

Referring now to FIG. 14, container 490 may for example be mounted on a wall 530, placed on a skid mount, or placed in another readily accessible area for refilling. Container 490 is preferably configured to hold a volume of hygienic fluid, and thus container 490 may be located near a sink or connected to a water line for mixing or diluting concentrated hygienic fluid. In any event, tubing 500 preferably extends from container 490 along wall 530 into and above the dropped ceiling, where as noted above it may terminate in one or more atomizer nozzles 510.

In operation, hygienic fluid within container 490 may be drawn through tubing 500 and dispersed at atomizer tips 510. This may be accomplished using a small motor or pump mounted above the dropped ceiling and in fluid communication with tubing 500, although those of skill in the art are familiar with other methods for drawing fluid from container 490. In some embodiments, the motor or pump may be configured to agitate the hygienic fluid where doing so is required prior to application, or container 490 may contain another suitable agitator. Moreover, fluid may be drawn from container 490 at preprogrammed times and/or manually. In this regard, the motor or pump may be in electrical communication with switch 40 and/or programmable timer 90, the functionality of which is described above with respect to UV disinfecting lighting system 20.

Figure 15:
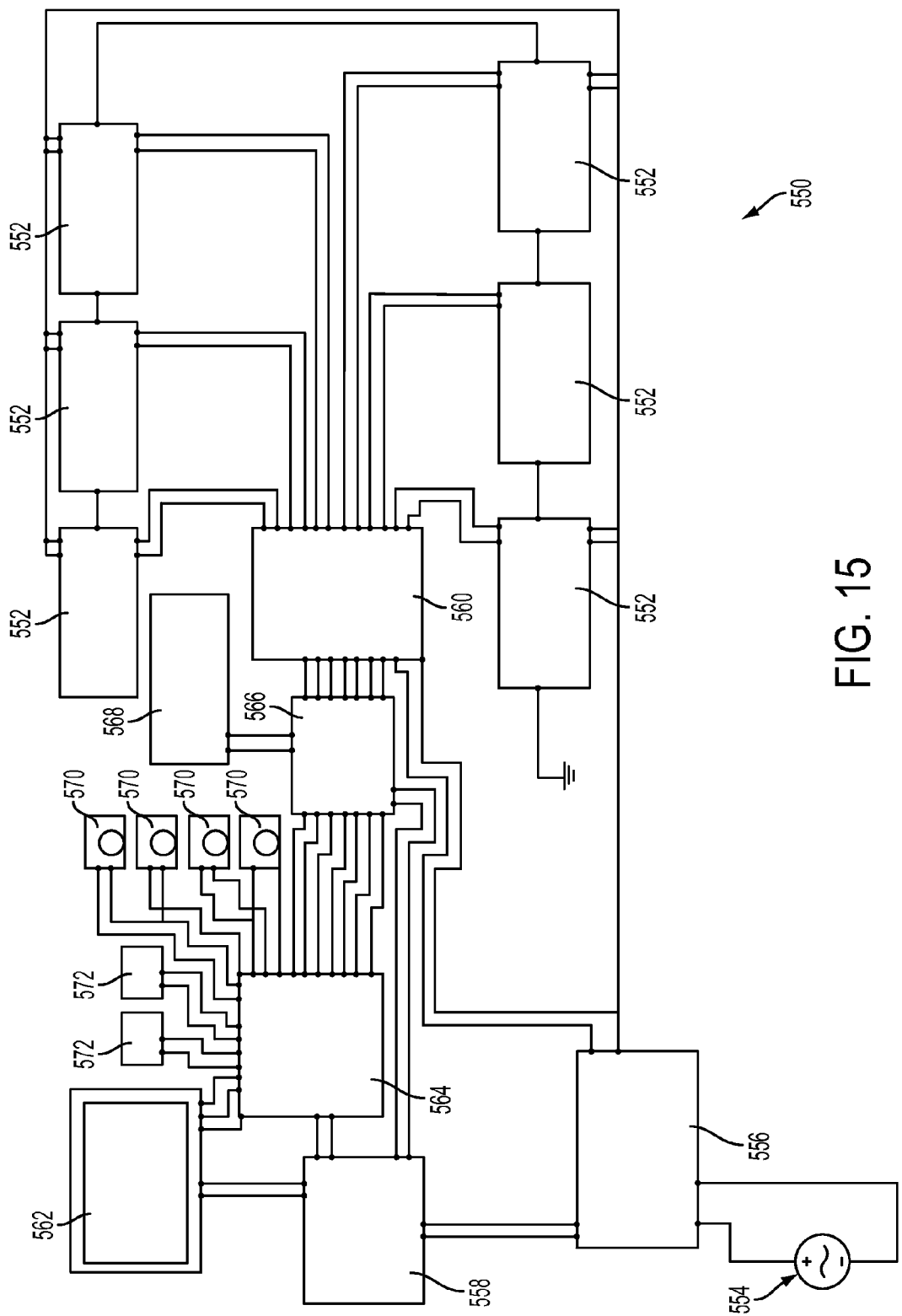
FIG. 15 is a simplified wiring diagram for a UV disinfecting lighting system in accordance with yet another embodiment of the present invention.

In embodiments of the present invention, a single control system may control a UV disinfecting lighting system that comprises a plurality of light fixtures. In some embodiments, the single control system may be operative to control up to or more than 28 fixtures. For example, FIG. 15 is a simplified wiring diagram for a UV disinfecting lighting system 550 in accordance with one embodiment of the present invention. In this embodiment, system 550 comprises six recessed troffer light fixtures 552. Recessed troffer light fixtures 552 may be similar in many respects to the various recessed troffers described above. As shown, mains power 554 is provided to a fuse panel 556, which is in electrical communication with a 5V/12V power supply 558, solid state relays 560, and light fixtures 552. Power supply 558 supplies power to an input device 562, a controller 564, and light fixtures 552 via transistors 566 in electrical communication with relays 560. An emergency stop button 568, also in electrical communication with power supply 558, may also be provided. As those of skill in the art will appreciate, emergency stop button 568 is preferably operative, when actuated by a user, to disable some or all UV lighting devices in system 550.

Controller 564 is in electrical communication with input device 562, transistors 566, push buttons 570, and sensors 572. Controller 564 may carry out the functional and control processing associated with system 550 and preferably comprises the hardware and software necessary to operate system 550 as described herein. In this regard, controller 564 may comprise one or more processors, microprocessors, programmable logic devices, or other processing components. In addition, controller 564 may comprise one or more volatile or non-volatile memory components that store information accessible to controller 564. Controller 564 is preferably operative to display a graphical user interface for controlling system 550 on input device 562, which may be an LCD screen in one embodiment. Push buttons 570 are operative to selectively actuate various lighting devices in light fixtures 552.

In this embodiment, sensors 572 may be passive infrared (PIR) sensors for detecting the presence of a person in the environment in which system 550 operates. Thus, sensors 572 are preferably sensitive to radiation at wavelengths emitted by humans, for example in the mid-infrared range. PIR sensors may be desirable for detecting the presence (and preventing UV irradiation) of a person who is in the environment but is also immobile, such as a sedated patient on an operating room table. In various embodiments, sensors 572 may be wall-mounted or mounted on one or more of light fixtures 552, as described above. In addition, although two such sensors 572 are shown, fewer or more than two sensors 572 may be provided in other embodiments. In one embodiment, sensors 572 may be similar to the PIR sensors offered by Panasonic Electric Works Corporation of America having part number AMN34111. In this embodiment, when sensors 572 detect the presence of a person in the environment in which system 550 operates, controller 564 is preferably operative to turn off any UV lighting devices in light fixtures 552.

Figure 16A:
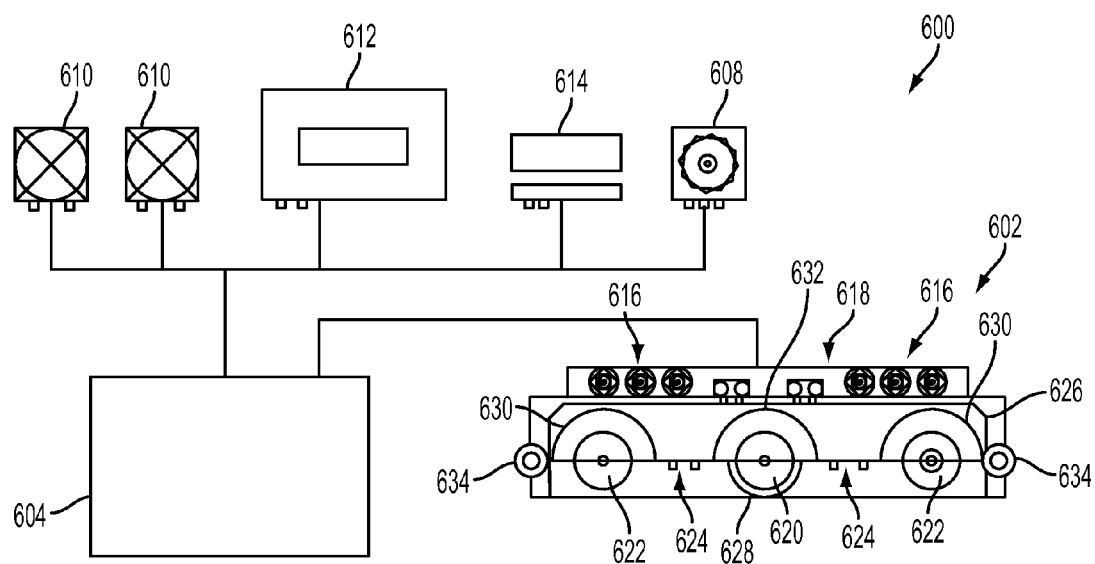
FIG. 16A is a schematic representation of a UV disinfecting lighting system in accordance with a further embodiment of the present invention.
Figure 16B:
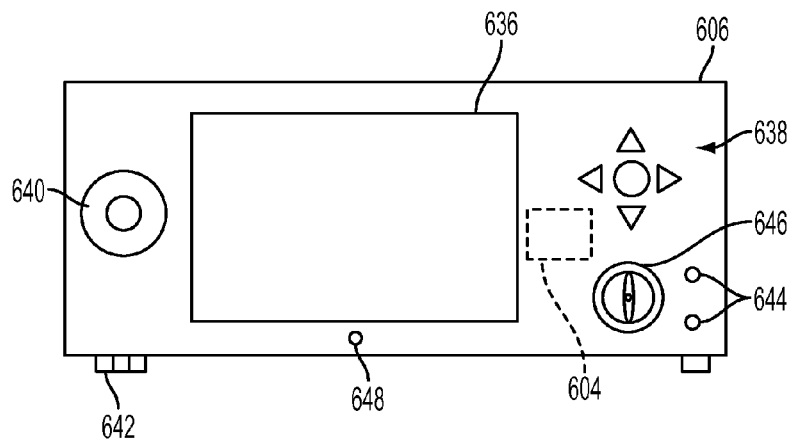
FIG. 16B is a schematic representation of a control panel which may operate in the UV disinfecting lighting system of FIG. 16A.

In some embodiments, rather than disabling UV irradiation when a person enters the environment in which a UV disinfecting lighting system operates, it may be desirable to provide substantially continuous UV radiation from a light fixture in the UV disinfecting lighting system regardless of whether a person has entered the environment. In this regard, FIG. 16A is a schematic representation of a UV disinfecting lighting system 600 in accordance with a further embodiment of the present invention, and FIG. 16B is a schematic representation of a control panel which may operate in system 600. Turning to these figures, system 600 comprises at least one recessed troffer light fixture 602 in electronic communication with a controller 604. (Although not illustrated in FIG. 16, system 600 may also comprise an atomizer system in some embodiments that is analogous to atomizer system 450 described with reference to FIGS. 13-14.)

Controller 604 may preferably be similar to controller 564, discussed above. In this embodiment, controller 604 may operate within a control panel 606, though controller 604 may be separate from control panel 606 in other embodiments. Controller 604 may be in wired or wireless electronic communication with light fixture 602, a rheostat 608, and a plurality of sensors, including PIR sensors 610, a motion sensor 612, and a door sensor 614. Sensors 610 and 612 are preferably respectively analogous to sensors 572 and 80, described above. Door sensor 614 is preferably operative to detect the opening of a door to the environment in which system 600 operates, which may signal the entry of a person. Thus, when door sensor 614 is actuated, controller 604 may preferably turn off any UV lighting devices then operating. Those of skill in the art are familiar with suitable sensors for door sensor 614, but in some embodiments sensor 614 may be a reed switch or another suitable magnetic sensor, such as those used in home intrusion detection systems.

Light fixture 602 may be similar in some respects to the recessed troffer light fixtures described above, and thus it may comprise one or more fans 616, one or more ballasts 618, and lighting devices 620, 622, and 624. In this embodiment, lighting devices 620 are analogous to lighting devices 50, lighting devices 622 are analogous to lighting devices 60, and lighting devices 624 are analogous to lighting devices 70. However, other embodiments may have any combination of lighting devices 620, 622, and/or 624. Lighting devices 620, 622, and 624 may be supported in fixture 602 via a lamp holder 626. Further, light fixture 602 may comprise a diffuser 628 in some embodiments that is supported beneath lighting devices 620.

The radiation emitted by lighting devices 620, 622, and/or 624 may be controlled via rheostat 608. As those of skill in the art will appreciate, rheostat 608 allows for dimming of lighting devices 620. Further, for lighting devices 622, 624, rheostat 608 may allow a user to adjust the amount of UV radiation to a desired level. In some embodiments, more than one rheostat 608 may be provided, for example one rheostat 608 for each type of lighting device in system 600.

Light fixture 602 may further comprise reflectors 630 that are selectively rotatable about each lighting device 622 and a reflector 632 disposed above lighting device 620. Reflectors 630, 632 may be generally semicircular, or "half-round," when viewed in cross-section, although this is not required, and may resemble a "half-cylinder" having a length substantially equal to the length of their associated lighting devices. Reflectors 630, 632 may each have a longitudinal axis which is collinear with or parallel to (but spaced apart from) the longitudinal axis of lighting devices 622, 620, respectively. Likewise, reflectors 630, 632, when viewed in cross-section, may have a diameter which is parallel with a plane containing the longitudinal axes of lighting devices 622, 620. It will be appreciated, however, that in some embodiments the shape of reflectors 630, 632 may be other than half-cylindrical or, in cross-section, half-round. For example, reflectors 630, 632 may be parabolic, half-oval, polygonal, or V-shaped in cross-section in other embodiments. Those of skill in the art can select an appropriate shape of reflectors 630, 632 by considering the desired angles of reflection, among other factors.

Reflectors 630, 632 may be formed from a quartz sleeve in some embodiments, though this is not required. In other embodiments, reflectors 630, 632 may be formed of a lightweight metal material, such as aluminum. Reflectors 630, 632 may comprise a reflective backing on the surface thereof that faces lighting devices 622, 620, respectively, to reflect radiation emitted from lighting devices 622, 620. In some embodiments, the reflective backing may be analogous to reflective backing 162 described above. Providing the reflective backing may increase the output of UV radiation by approximately 40-50% in some embodiments.

Notably, in this embodiment, reflectors 630 are preferably rotatable about their longitudinal axes and, consequently, about lighting devices 622. In particular, reflectors 630 may be operatively connected to, and driven by, one or more motors 634. In some embodiments, motors 634 may be servo-controlled motors. In any event, motors 634 are preferably in electronic communication with and controlled by controller 604. Thus, controller 604 may actuate motors 634 to cause rotation of reflectors 630 at predetermined times or upon the receipt of a signal from one of sensors 610, 612, or 614. In other embodiments, reflector 632 may also be rotatable.

Accordingly, system 600 may provide substantially continuous UV radiation from a light fixture in the UV disinfecting lighting system regardless of whether a person has entered the environment. Specifically, in the illustrated embodiment, reflectors 630 may be rotatable between a first position wherein they are positioned directly above lighting devices 622, as shown in FIG. 16A, and a second position wherein they are directly below lighting devices 622 (i.e., rotated 180° from the position shown in FIG. 16A), in response to a person entering the environment in which system 600 operates. Again, because of the cumulative effect of UV radiation, use of rotatable reflectors 630 may not reduce the germicidal effectiveness of system 600. In other embodiments, reflectors 630 may be rotatable 360° about their longitudinal axes so that they may be positioned at any angle relative to lighting devices 622, as needed or desired.

In other words, if lighting devices 622 are in operation, and if controller 604 receives a signal from one of sensors 610, 612, or 614 indicative of a person entering the environment, controller 604 may cause rotation of reflectors 630 to the second position. However, controller 604 may also allow lighting devices 622 to remain operational, rather than turning them off as described above with reference to other embodiments. Thereby, reflectors 630 may shield the person entering the environment from direct exposure to UV radiation, but lighting devices 622 remain in operation to continue inactivation of microorganisms. Specifically, UV radiation is reflected back toward light fixture 602 and thus, when reflectors 630 are in this position, lighting devices 622 may inactivate microorganisms in the air and on the various surfaces of light fixture 602 itself. In some embodiments, when controller 604 causes rotation of reflectors 630, it may at the same time actuate fans 616. Fans 616 may draw air toward lighting devices 622 to facilitate sterilization of the air of the environment in which system 600 operates.

When sensors 610-14 no longer detect the presence of a person in the vicinity of system 600, controller 604 may cause rotation of reflectors 630 back to the position shown in FIG. 16A. Thus, lighting devices 622 may again provide direct UV radiation of air and surfaces below light fixture 602, as it has been determined that it is safe to do so. Based on the above, it will be appreciated that system 600 may provide for multiple cycles of direct UV radiation of the surfaces below light fixture 602 throughout the course of a day (depending on the size of the room and the frequency of its use) and may likewise provide continuous UV radiation of the air about light fixture 602. Accordingly, in some embodiments of system 600, lighting devices 624 may not be provided.

In other embodiments, when controller 604 receives a signal indicative of entry into the environment of system 600, controller 604 may briefly deactivate lighting devices 622, for example for a length of time sufficient for reflectors 630 to rotate between the first and second positions. This brief deactivation period (e.g., a matter of seconds) may prevent inadvertent exposure to UV radiation, and lighting devices 622 may be reactivated as soon as reflectors 630 have reached the second position. Although brief deactivation of lighting devices 622 occurs in these embodiments, system 600 may still provide substantially continuous direct and indirect UV radiation for inactivating microorganisms both on surfaces beneath light fixture 602 and in the air. Moreover, the cumulative effect of UV radiation allows system 600 to remain its germicidal effectiveness, as noted above. In still other embodiments, where persons do not enter the environment of system 600 for a long period of time, controller 604 may be programmed to deactivate lighting devices 622 after more than a predetermined amount of direct UV irradiation (e.g., 15 or 30 minutes or more), depending on the microorganisms targeted and the desired dosage.

In an alternative embodiment, reflectors 630 may not be provided in light fixture 602. Rather, a portion of lighting devices 622 may be covered with a reflective material, and the lighting devices 622 themselves are rotatable about their longitudinal axes. The operation of this embodiment is similar to the operation of reflectors 630, described above. In a still further embodiment, light fixture 602 may comprise doors or flaps pivotably connected to opposing sides of fixture 602. The doors or flaps may operatively connected to and driven by motor(s) 634, or in some embodiments they may be manually operated. As described above, when controller 604 receives a signal indicative of entry into the environment of system 600, controller 604 would actuate motor(s) 634 to cause the doors to close, thereby shielding a person from direct exposure to UV radiation. At the same time, fans 616 would be actuated to draw air into and/or circulate air through light fixture 602, wherein microorganisms are still inactivated.

In yet another embodiment, light fixtures 602 may also be mounted on or installed in a wall of a given environment in which it is desired to inactivate microorganisms. Such light fixtures 602 may be used in conjunction with other light fixtures 602 that are suspended from the ceiling to provide UV radiation from multiple directions. The operation of light fixture 602 in this embodiment may preferably be the same as described above. When light fixture 602 is mounted on a wall, lighting devices 620 may not be provided, but lighting devices 622 and/or 624 are preferably provided. It will be appreciated that it may be desirable to install light fixture 620 in a wall near the floor in some embodiments to provide UV radiation to areas that may otherwise be shielded from overhead UV irradiation (e.g., in a "shadow").

Moreover, in some embodiments, light fixture 602 may be provided with one or more ionizers for purification of the air in the environment in which system 600 is located and for facilitating removal of smoke and odors. Although many environments may be provided with ductwork-based ionizers, such ionizers do not have as much air purifying capacity as room-based ionizers. In particular, with ductwork-based ionizers, because ionized air molecules do not travel far, the ionized molecules may attach to the walls of the ductwork rather than purifying the air in the environment. Thus, coupling an ionizer with light fixture 602 may provide greater air purification. For example, the one or more ionizers may be disposed on the housing of light fixture 602 and centered above each lighting device thereof. Those of skill in the art are familiar with commercially-available ionizers suitable for this purpose and which in some embodiments may be analogous to the ionizers utilized in air purification systems. In one example, the ionizer may negatively ionize air molecules, which then may attach to airborne particles. The ionizer may comprise a charged collector plate to attract and collect the ionized airborne particles. The ionizer may be fanless, but in one embodiment, the ionizer may cooperate with fans 616 and atomizer system 450 (where provided).

In still other embodiments, light fixture 602 may be provided with a plurality of bristles to prevent accumulation of dust thereon. For example, a plurality of bristles may formed of a suitable conductive material may be coupled with a conductive strip of metal material, such as aluminum. The metal material may be coupled with the housing of light fixture 602 and grounded. As a result, the grounded conductive bristles may draw the static charge off of lighting devices of light fixture 602. In one embodiment, the conductive bristles may be analogous to conductive bristle configurations found in a printer to draw static off of paper.

Additional features of system 600 are discussed with reference to FIG. 16B. Control panel 606 preferably comprises an input device 636, which in one embodiment may be a touchscreen. A keypad 638 and an emergency stop button 640 may also be provided. Control panel 606 may be in wired or wireless communication with the components of system 600, and thus control panel 606 preferably comprises electronics operative to enable wireless radio-frequency communication according to standards familiar to those of skill in the art, such as the IEEE 802.11, 3G, 4G, or LTE standards. Thus, for example, a suitable smartphone or tablet application (e.g., an Apple or Android application) may be used to remotely manage operations of system 600 via communication with control panel 606. Further, control panel 606 may comprise a data connection 642, which may be any suitable hardware interface for transferring data regarding system 600, such as (but not limited to) an Ethernet connection.

Control panel 606 may also include LED indicators 644 that indicate the status of system 600 or components therein. Indicators 644 may be configured to illuminate in various colors, such as red and green, depending on the status of system 600 or a component therein. Also, a key switch 646 may be provided. In one embodiment, system 600 may not operate until a user having the corresponding key turns key switch 646 to the "on" position. Further, system 600 may comprise an alarm that sounds upon the occurrence of various predefined conditions, such as when UV lighting devices are turned off. A piezo speaker or buzzer 648 may also be provided to sound when interlock faults occur.

Figures 17B, 17C:
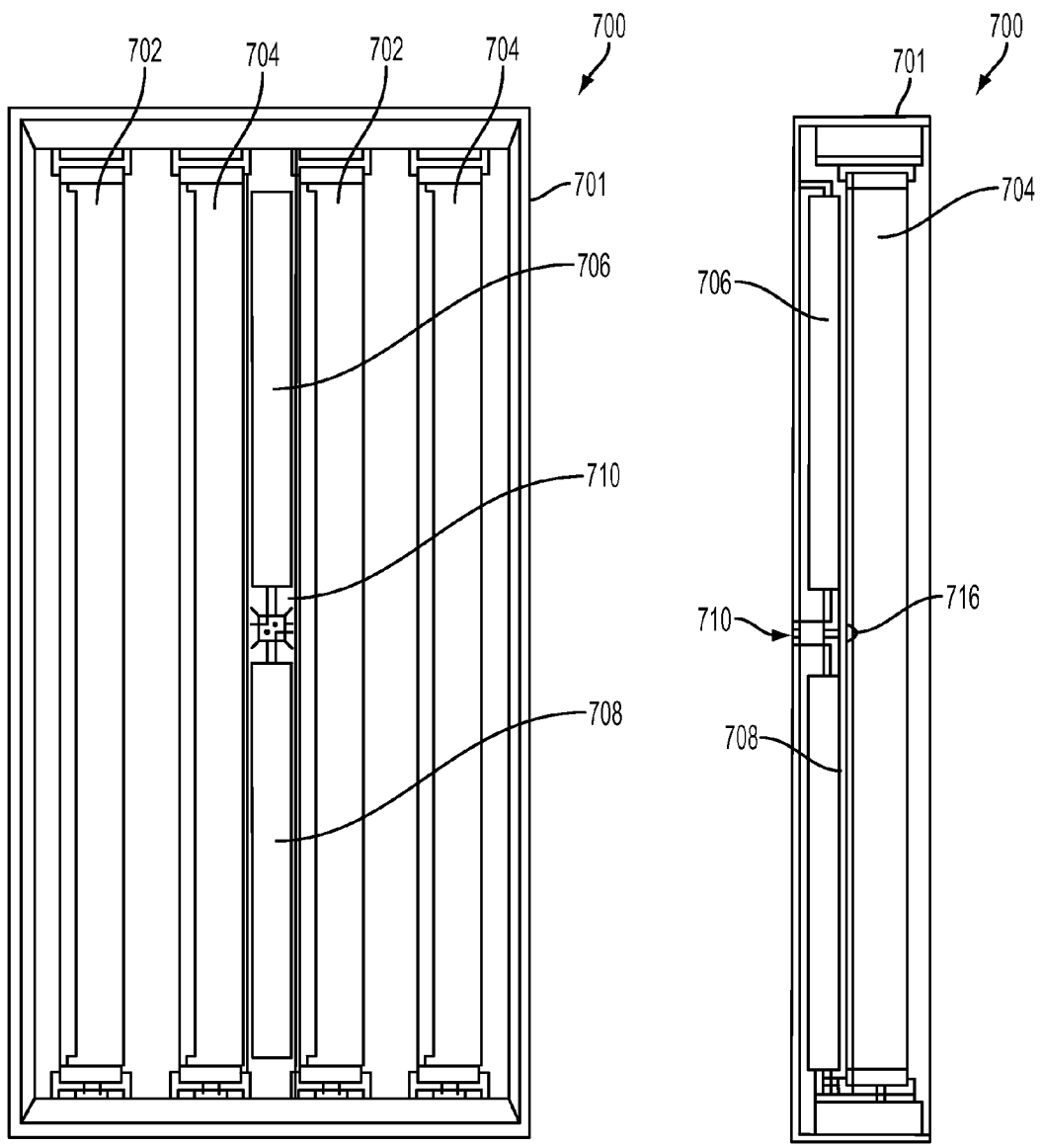
FIG. 17B is a schematic top plan view of the recessed troffer light fixture of FIG. 17A shown without reflectors or diffusers.
FIG. 17C is a schematic cross-sectional side view of the recessed troffer light fixture of FIG. 17A shown without reflectors or diffusers.

FIGS. 17A-C are schematic elevation, top plan, and side views of a recessed troffer light fixture 700 in accordance with another embodiment of the present invention. Light fixture 700 may be similar in some respects to the recessed troffer light fixtures described above, but modified as discussed below. Here, light fixture 700 comprises a housing 701 in which two lighting devices 702 and two lighting devices 704 are supported. Lighting devices 702 may be operative to emit visible radiation, and lighting devices 704 may be operative to emit ultraviolet radiation. Further, light fixture 700 may comprise a ballast 706 operative to drive lighting devices 702 and a ballast 708 operative to drive lighting devices 704. A connector 710 may be provided on a top surface of housing 701 of light fixture 700 for providing electrical power and communication with a controller.

As best seen in FIG. 17A, light fixture 700 may also comprise reflectors 712 disposed above each of lighting devices 702, 704. In this embodiment, reflectors 712 may define, in cross-section, a half-decagon shape. Further, reflectors 712 may be coupled with diffusers 714 disposed directly beneath each of lighting devices 702, 704. In some embodiments, reflectors 712 and, correspondingly, diffusers 714 may be rotatable about each of lighting devices 702, 704, as described above. Additionally, in this embodiment, a PIR sensor 716, which may be analogous to PIR sensors 572, may be coupled with housing 701.

Figure 18:
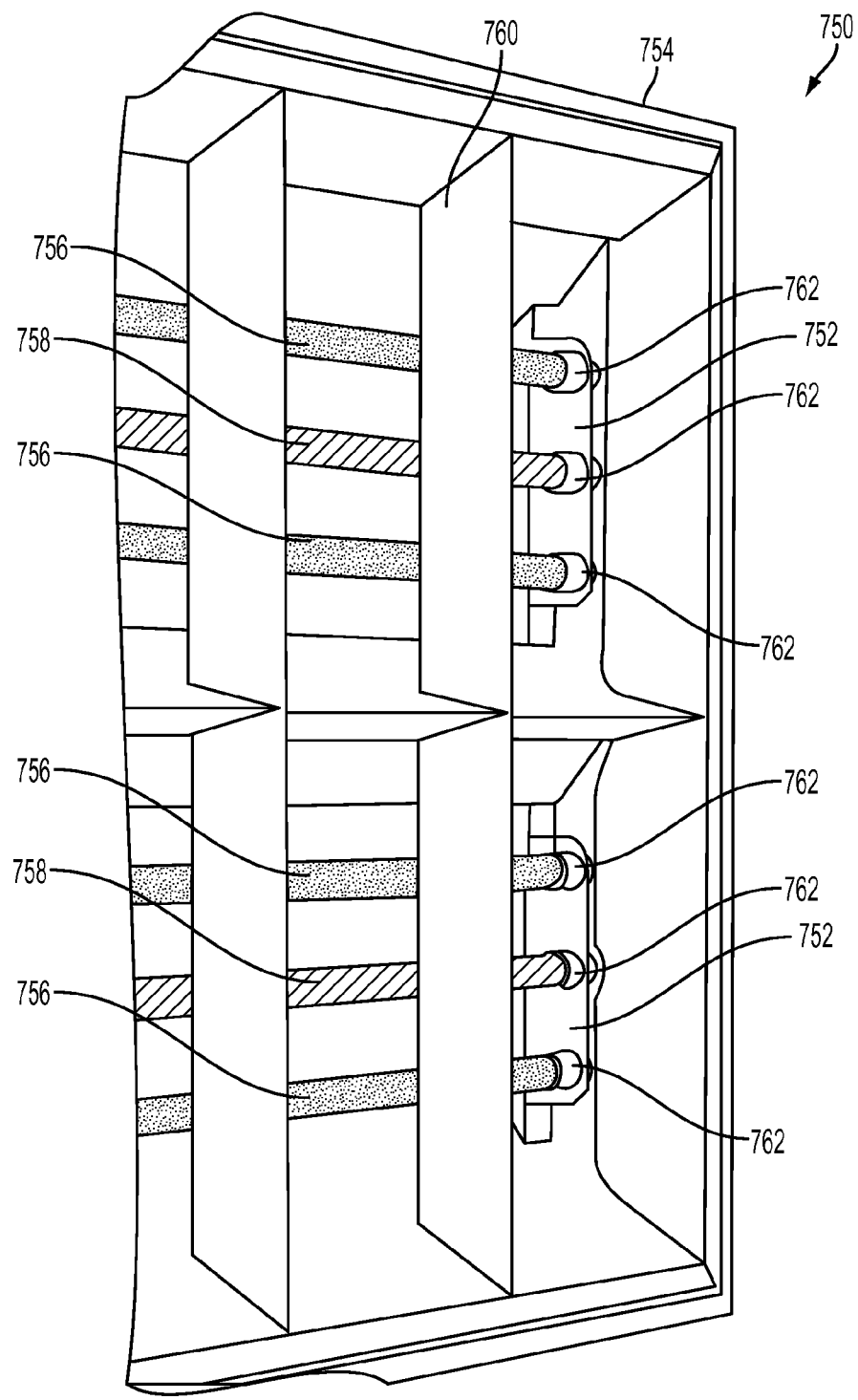
FIG. 18 is a partial perspective view of a recessed troffer light fixture comprising lamp holders which support a plurality of lighting devices therein according to yet another embodiment of the present invention.

As noted above, in some embodiments lighting devices may be supported in a light fixture via a lamp holder. In this regard, FIG. 18 is a partial perspective view of a recessed troffer light fixture 750 comprising lamp holders 752 which support a plurality of lighting devices therein. In this embodiment, light fixture 750 comprises a housing 754 in which four lighting devices 756 are supported and in which two lighting devices 758 are supported. Lighting devices 756 may be operative to emit visible radiation, and lighting devices 758 may be operative to emit ultraviolet radiation. Light fixture 750 may also comprise a parabolic reflector grid 760, which may be analogous to parabolic reflector grid 150 described above.

As shown, lamp holders 752 may comprise a relatively thin, generally rectangular body portion which depends from (and is coupled with) an upper surface of housing 754. Lamp holders 752 may preferably be formed of any material suitable for supporting lighting devices in a lighting fixture, but in some embodiments lamp holders 752 may be formed of a lightweight metal material, such as steel or aluminum. Lamp holders 752 may preferably be coupled with housing 754 proximate the sockets for each lighting device in housing 754. Although not shown in FIG. 18, additional lamp holders may also be disposed in facing opposition to lamp holders 752 at the opposite side of light fixture 750 to support the other ends of lighting devices 756, 758.

A plurality of apertures 762 are defined through each of lamp holders 752. In the illustrated embodiment, for example, each lamp holder 752 defines three apertures 762. Apertures 762 are preferably sized to receive an end or connector portion of each lighting device 756, 758 therethrough. Thus, each lamp holder 752 may support multiple lighting devices 756 or 758. Lamp holders 752 may be coupled with housing 754 using suitable fasteners, such as bolts or screws.

It can thus be seen that embodiments of the present invention provide a novel UV disinfecting lighting system comprising at least one UV lighting device configured to provide germicidal irradiation of the air about the lighting system and at least one UV lighting device configured to provide germicidal irradiation of at least one surface below the lamp. In embodiments of the invention which also comprise fluorescent lamps for illumination, it will be appreciated that UV disinfecting lighting system may achieve substantial energy savings. These are in addition to the health care savings offered by the use of germicidal UV lighting devices. While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the scope and spirit thereof.

What is claimed is:

1. A germicidal light fixture, comprising:
    a support structure;
    at least one ultraviolet fluorescent lamp coupled with said support structure operative to emit ultraviolet radiation at a first predetermined wavelength;
    at least one ultraviolet light-emitting diode coupled with said support structure operative to emit ultraviolet radiation at a second predetermined wavelength;
    wherein said first and second predetermined wavelengths are selected such that ultraviolet radiation emitted from said at least one first lighting device and from said at least one second lighting device, respectively, is operative to inactivate microorganisms; and
    at least one third lighting device coupled with said support structure operative to emit visible radiation.

2. The germicidal light fixture of claim 1, wherein said first predetermined wavelength is equal to said second predetermined wavelength.

3. The germicidal light fixture of claim 1, wherein said first predetermined wavelength is approximately 253.7 nanometers.

4. The germicidal light fixture of claim 1, wherein said at least one third lighting device is a fluorescent lighting device.

5. The germicidal light fixture of claim 1, wherein said visible radiation has a wavelength in the range of about 400 nanometers to about 700 nanometers.

6. The germicidal light fixture of claim 1, said support structure comprising a reflective backing.

7. A germicidal light fixture system, comprising:
    a support structure;
    a controller;
    at least one presence detection sensor in electronic communication with said controller, said at least one presence detection sensor operative to transmit a signal to said controller indicative of the presence of a person;
    at least one first lighting device coupled with said support structure operative to emit ultraviolet radiation at a first predetermined wavelength, said first predetermined wavelength selected such that the ultraviolet radiation emitted from said at least one first lighting device is operative to inactivate microorganisms;
    said at least one first lighting device having a first longitudinal axis;
    at least one reflector coupled with said support structure, said at least one reflector having a second longitudinal axis parallel with said first longitudinal axis; and
    said at least one reflector being rotatable about said first longitudinal axis in response to said signal.

8. The germicidal light fixture system of claim 7, further comprising at least one second lighting device coupled with said support structure operative to emit ultraviolet radiation at a second predetermined wavelength, said second predetermined wavelength selected such that the ultraviolet radiation emitted from said at least one second lighting device is operative to inactivate microorganisms.

9. The germicidal light fixture system of claim 8, wherein said at least one second lighting device is an ultraviolet light-emitting diode.

10. The germicidal light fixture system of claim 7, further comprising at least one third lighting device coupled with said support structure operative to emit visible radiation.

11. The germicidal light fixture system of claim 7, wherein said at least one presence detection sensor is a motion sensor.

12. The germicidal light fixture system of claim 7, wherein said at least one reflector is formed of a quartz sleeve.

13. The germicidal light fixture system of claim 7, wherein said at least one reflector is half-cylindrical in shape.

14. A germicidal light fixture system, comprising:
    a support structure;
    a controller in electronic communication with said support structure;
    at least one presence detection sensor in electronic communication with said controller, said at least one presence detection sensor operative to transmit a signal to said controller indicative of the presence of a person;
    at least one first lighting device coupled with said support structure operative to emit ultraviolet radiation at a first predetermined wavelength;
    at least one second lighting device coupled with said support structure operative to emit ultraviolet radiation at a second predetermined wavelength different from the first predetermined wavelength;
    wherein said first and second predetermined wavelengths are selected such that the ultraviolet radiation emitted from said at least one first lighting device and from said at least one second lighting device, respectively, is operative to inactivate microorganisms; and
    said controller operative to deactivate said at least one first lighting device in response to said signal.

15. The germicidal light fixture system of claim 14, further comprising a programmable timer in electrical communication with said controller.

16. The germicidal light fixture system of claim 14, further comprising at least one third lighting device coupled with said support structure operative to emit visible radiation.

17. The germicidal light fixture system of claim 14, further comprising at least one air-moving device coupled with said support structure.

18. A germicidal light fixture, comprising:
    a support structure;
    at least one first lighting device coupled with said support structure operative to emit ultraviolet radiation at a first predetermined wavelength, said first predetermined wavelength selected such that the ultraviolet radiation emitted from said at least one first lighting device is operative to inactivate microorganisms;

said at least one first lighting device having a first longitudinal axis;
at least one reflector coupled with said support structure, said at least one reflector having a second longitudinal axis parallel with said first longitudinal axis; and
said at least one reflector being rotatable about said first longitudinal axis.

19. The germicidal light fixture of claim 18, further comprising at least one second lighting device coupled with said support structure operative to emit visible radiation.

20. The germicidal light fixture of claim 18, further comprising at least one ionizer coupled with said support structure.

\* \* \* \* \*